US012606617B2

(12) United States Patent
Spicer et al.

(10) Patent No.: US 12,606,617 B2
(45) Date of Patent: Apr. 21, 2026

(54) COMPOSITION COMPRISING AN IgE ANTIBODY

(71) Applicant: King's College London, London (GB)

(72) Inventors: James Spicer, London (GB); Sophia Karagiannis, London (GB); Mariangela Figini, London (GB); Hannah Gould, London (GB)

(73) Assignee: Kings's College London, London (GB)

( * ) Notice: Subject to any disclaimer, the term of this patent is extended or adjusted under 35 U.S.C. 154(b) by 715 days.

(21) Appl. No.: 17/919,589

(22) PCT Filed: Apr. 23, 2021

(86) PCT No.: PCT/EP2021/060749
§ 371 (c)(1),
(2) Date: Oct. 18, 2022

(87) PCT Pub. No.: WO2021/214329
PCT Pub. Date: Oct. 28, 2021

(65) Prior Publication Data
US 2023/0151090 A1      May 18, 2023

(30) Foreign Application Priority Data
Apr. 24, 2020    (GB) ..................................... 2006093

(51) Int. Cl.
*C07K 16/28*        (2006.01)
*A61P 35/00*        (2006.01)
A61K 39/00          (2006.01)

(52) U.S. Cl.
CPC .............. *C07K 16/28* (2013.01); *A61P 35/00* (2018.01); *A61K 2039/505* (2013.01); *A61K 2039/545* (2013.01); *C07K 2317/24* (2013.01); *C07K 2317/52* (2013.01); *C07K 2317/732* (2013.01)

(58) Field of Classification Search
CPC ................ C07K 16/28; C07K 2317/94; C07K 2317/73; A61P 35/00; A61K 2039/505; A61K 2039/545
See application file for complete search history.

(56) References Cited

U.S. PATENT DOCUMENTS

| | | |
|---|---|---|
| 4,458,066 A | 7/1984 | Caruthers et al. |
| 5,565,332 A | 10/1996 | Hoggenboom et al. |
| 5,585,089 A | 12/1996 | Queen et al. |
| 5,807,715 A | 9/1998 | Morrison et al. |

FOREIGN PATENT DOCUMENTS

| | | |
|---|---|---|
| WO | WO 2013/050725 | 4/2013 |
| WO | WO 2015/173782 | 11/2015 |

OTHER PUBLICATIONS

Baxevanis, CN, "Antibody-based cancer therapy", 2008, Expert Opin. Drug Discov., 3(4), 441-452. (Year: 2008).*
Hjelm, B et. al. "Parallel Immunizations of Rabbits Using the Same Antigen Yield Antibodies with Similar, but Not Identical, Epitopes", 2012, PLOS One, 7(12), 1-12. (Year: 2012).*
Gould et. al. "Comparison of IgE and IgG antibody-dependent cytotoxicity in vitro and in a SCID mouse xenograft model of ovarian carcinoma", Eur. J. Immunol., 1999, 29, 3527-3537. (Year: 1999).*
Karagiannis et. al. "Activity of human monocytes in IgE antibody-dependent surveillance and killing of ovarian tumor cells", Eur. J. Immunol., 2003, 33, 1030-1040. (Year: 2003).*
Josephs D.H., et al., "An Immunologically Relevant Rodent Model Demonstrates Safety of Therapy Using a Tumour-specific IgE," Allergy, Dec. 2018, vol. 73, No. 12, pp. 2328-2341.
Van Zanten-Przybysz I., et al., "Cellular and Humoral Responses after Multiple Injections of Unconjugated Chimeric Monoclonal Antibody M0V18 in Ovarian Cancer Patients: A Pilot Study", Journal of Cancer Research and Clinical Oncology, vol. 128, No. 9, Aug. 23, 2002, pp. 484-492.
International Search Report and Written Opinion for PCT/EP2021/060749. Mailed Jul. 22, 2021. 14 pages.
Alduaij et al., The future of anti-CD20 monoclonal antibodies: are we making progress? Blood. Mar. 17, 2011;117(11):2993-3001.
Altschul et al., Basic local alignment search tool. J Mol Biol. Oct. 5, 1990;215(3):403-10.
Altschul et al., Issues in searching molecular sequence databases. Nat Genet. Feb. 1994;6(2):119-29.
Ausubel et al., Current Protocols in Molecular Biology. John Wiley & Sons, Inc. 1994. TOC only. 14 pages.
Barany and Merrifield, "Solid-phase peptide synthesis" in The Peptides: Analysis, Synthesis, Biology. vol. 2: Special Methods in Peptide Synthesis, Part A. Academic Press, Inc. 1979, TOC only.
Beaucage et al., Deoxynucleoside phosphoramidites—A new class of key intermediates for deoxypolynucleotide synthesis. Tetrahedron Letters, 1981, 22(20), 1859-1862.
Beutier et al., IgG subclasses determine pathways of anaphylaxis in mice. J Allergy Clin Immunol. Jan. 2017; 139(1):269-280.e7.
Brown et al., Chemical synthesis and cloning of a tyrosine tRNA gene. Methods Enzymol. 1979:68:109-51.
Bruggemann et al., Comparison of the effector functions of human immunoglobulins using a matched set of chimeric antibodies. J Exp Med. Nov. 1, 1987;166(5):1351-61.

(Continued)

*Primary Examiner* — Laura B Goddard
*Assistant Examiner* — Alyssa Rae Stonebraker
(74) *Attorney, Agent, or Firm* — Casimir Jones, SC; Thomas A. Isenbarger

(57)      ABSTRACT

In one aspect, the present invention relates to a pharmaceutical unit dosage composition comprising an antibody of isotype immunoglobulin E (IgE), wherein the composition comprises less than 50 mg of the IgE antibody. The pharmaceutical unit dosage compositions may be administered to a mammalian subject and find use in treating cancer, in particular, human ovarian cancers.

21 Claims, 5 Drawing Sheets

Specification includes a Sequence Listing.

(56)                    References Cited

OTHER PUBLICATIONS

Buchner et al., A method for increasing the yield of properly folded recombinant fusion proteins: single-chain immunotoxins from renaturation of bacterial inclusion bodies. Anal Biochem. Sep. 1992;205(2):263-70.

Carter et al., Humanization of an anti-p185HER2 antibody for human cancer therapy. Proc Natl Acad Sci U S A. May 15, 1992;89(10):4285-9.

Chothia et al., Canonical structures for the hypervariable regions of immunoglobulins. J Mol Biol. Aug. 20, 1987;196(4):901-17.

Coney et al., Cloning of a tumor-associated antigen: MOv18 and MOv19 antibodies recognize a folate-binding protein. Cancer Res. Nov. 15, 1991;51(22):6125-32.

Corpet. Multiple sequence alignment with hierarchical clustering. Nucleic Acids Res. Nov. 25, 1988;16(22):10881-90.

Dechant et al., IgA antibodies for cancer therapy. Crit Rev Oncol Hematol. Jul.-Aug. 2001;39(1-2):69-77.

Dondelinger et al., Understanding the Significance and Implications of Antibody Numbering and Antigen-Binding Surface/Residue Definition. Front Immunol. Oct. 16, 2018:9:2278. 15 pages.

Eisenhauer et al., New response evaluation criteria in solid tumours: revised Recist guideline (version 1.1). Eur J Cancer. Jan. 2009;45(2):228-47.

Giudicelli et al., IMGT, the international ImMunoGeneTics database. Nucleic Acids Res. Jan. 1, 1997;25(1):206-11.

Gluzman ed., Eukaryotic Viral Vectors, Cold Spring Harbor Laboratory, 1982. TOC only. 6 pages.

Goto et al., Human high molecular weight-melanoma-associated antigen: utility for detection of metastatic melanoma in sentinel lymph nodes. Clin Cancer Res. Jun. 1, 2008;14(11):3401-7.

Gould et al., Comparison of IgE and IgG antibody-dependent cytotoxicity in vitro and in a SCID mouse xenograft model of ovarian carcinoma. Eur J Immunol. Nov. 1999;29(11):3527-37.

Helm et al., The mast cell binding site on human immunoglobulin E. Nature. Jan. 14, 1988;331(6152):180-3.

Hendrikx et al., Fixed Dosing of Monoclonal Antibodies in Oncology. Oncologist. Oct. 2017;22(10):1212-1221.

Higgins et al., Clustal: a package for performing multiple sequence alignment on a microcomputer. Gene. Dec. 15, 1988;73(1):237-44.

Higgins et al., Fast and sensitive multiple sequence alignments on a microcomputer. Comput Appl Biosci. Apr. 1989;5(2):151-3.

Huse et al., Generation of a large combinatorial library of the immunoglobulin repertoire in phage lambda. Science. Dec. 8, 1989;246(4935):1275-81.

IMGT data base. http://www.imgt.org/IMGT_GENE-DB/GENElect?query=2+IGHE&species=Homo+sapiens. Retrieved Mar. 19, 2024. 15 pages.

International ImMunoGeneTics Information System (IMGT®) website at http://www.imgt.org. Retrieved Mar. 19, 2024. 1 page.

Jones et al., Replacing the complementarity-determining regions in a human antibody with those from a mouse. Nature. 1986;321(6069):522-5.

Josephs et al., Anti-Folate Receptor-α IgE but not IgG Recruits Macrophages to Attack Tumors via TNFα/MCP-1 Signaling. Cancer Res. Mar. 1, 2017;77(5):1127-1141.

Kabat et al. (U.S.) NI of H. Sequences of Immunoglobulin Chains: Tabulation Analysis of Amino Acid Sequences of Precursors, V-regions, C-regions, J-Chain BP-Microglobulins, 1979, TOC only. 2 pages.

Kabat et al., Sequences of Proteins of Immunological Interest, U.S. Department of Health and Human Services, 1991. TOC only. 13 pages.

Karagiannis et al., Activity of human monocytes in IgE antibody-dependent surveillance and killing of ovarian tumor cells. Eur J Immunol. Apr. 2003;33(4):1030-40.

Karagiannis et al., IgE-antibody-dependent immunotherapy of solid tumors: cytotoxic and phagocytic mechanisms of eradication of ovarian cancer cells. J Immunol. Sep. 1, 2007;179(5):2832-43.

Karagiannis et al., Recombinant IgE antibodies for passive immunotherapy of solid tumours: from concept towards clinical application. Cancer Immunol Immunother. Sep. 2012;61(9):1547-64.

Karagiannis et al., Therapeutic IgE Antibodies: Harnessing a Macrophage-Mediated Immune Surveillance Mechanism against Cancer. Cancer Res. Jun. 1, 2017;77(11):2779-2783.

Kohler et al., Continuous cultures of fused cells secreting antibody of predefined specificity. Nature. Aug. 7, 1975;256(5517):495-7.

Kuby. Immunology, 3rd Ed., W.H. Freeman & Co., New York, 1997. TOC only. 12 pages.

Kuppers. Molecular single-cell PCR analysis of rearranged immunoglobulin genes as a tool to determine the clonal composition of normal and malignant human B cells. Methods Mol Biol. 2004:271:225-38.

Kurowsawa et al., Target-selective homologous recombination cloning for high-throughput generation of monoclonal antibodies from single plasma cells. BMC Biotechnol. Apr. 13, 2011:11:39. 8 pages.

Lee et al., Molecular mechanism of PD-1/PD-L1 blockade via anti-PD-L1 antibodies atezolizumab and durvalumab. Sci Rep. Jul. 17, 2017;7(1):5532. 1-12.

Lefranc. Unique database numbering system for immunogenetic analysis. Immunol Today. Nov. 1997;18(11):509.

Leoh et al., IgE immunotherapy against cancer. Curr Top Microbiol Immunol. 2015:388:109-49.

Lim et al., Structural Biology of the TNFα Antagonists Used in the Treatment of Rheumatoid Arthritis. Int J Mol Sci. Mar. 7, 2018;19(3):768. 14 pages.

Ling et al., Effect of VH-VL Families in Pertuzumab and Trastuzumab Recombinant Production, Her2 and FcγIIA Binding. Front Immunol. Mar. 12, 2018:9:469. 11 pages.

Magdelaine-Beuzelin et al., Structure-function relationships of the variable domains of monoclonal antibodies approved for cancer treatment. Crit Rev Oncol Hematol. Dec. 2007;64(3):210-25.

Mcdonnell et al., The structure of the IgE Cepsilon2 domain and its role in stabilizing the complex with its high-affinity receptor FcepsilonRlalpha. Nat Struct Biol. May 2001;8(5):437-41.

Merrifield et al., Solid Phase Peptide Synthesis. I. The Synthesis of a Tetrapeptide. J. Am. Chem. Soc. 1963, 85:2149-2156.

Narang et al., Improved phosphotriester Method for the Synthesis of Gene Fragments. Meth. Enzymol. 1979; 68:90-99.

Needham-Vandevanter et al., Characterization of an adduct between CC-1065 and a defined oligodeoxynucleotide duplex. Nucleic Acids Res. Aug. 10, 1984;12(15):6159-68.

Needleman et al., A general method applicable to the search for similarities in the amino acid sequence of two proteins. J Mol Biol. Mar. 1970;48(3):443-53.

Pearson et al., Improved tools for biological sequence comparison. Proc Natl Acad Sci U S A. Apr. 1988;85(8):2444-8.

Pluckthun. Antibody engineering: advances from the use of *Escherichia coli* expression systems. Biotechnology (N Y). Jun. 1991;9(6):545-51.

Remington's Pharmaceutical Science, Mack Publishing Company, Easton, Pa. 1985. TOC only. 4 pages.

Riechmann et al., Reshaping human antibodies for therapy. Nature. Mar. 24, 1988;332(6162):323-7.

Rustin et al., Defining response of ovarian carcinoma to initial chemotherapy according to serum CA 125. J Clin Oncol. May 1996;14(5):1545-51.

Sambrook et al., Molecular Cloning: A Laboratory Manual, 2nd ed., Cold Spring Harbor Laboratory Press, Cold Spring Harbor, N.Y., 1989. TOC only. 30 pages.

Sandhu. Protein engineering of antibodies. Crit Rev Biotechnol. 1992;12(5-6):437-62.

Saxena et al., Formation of three-dimensional structure in proteins. I. Rapid nonenzymic reactivation of reduced lysozyme. Biochemistry 1970, 9, 25, 5015-5023.

Scheeren et al., Antigen-specific monoclonal antibodies isolated from B cells expressing constitutively active STAT5. PLoS One. Apr. 15, 2011;6(4):e17189. 7 pages.

Schroter et al., A generic approach to engineer antibody pH-switches using combinatorial histidine scanning libraries and yeast display. MAbs. 2015;7(1):138-51.

(56) References Cited

OTHER PUBLICATIONS

Scopes. Protein Purification, Springer-Verlag, N.Y., 1994, TOC only. 17 pages.

Singer et al., Optimal humanization of 1B4, an anti-CD18 murine monoclonal antibody, is achieved by correct choice of human V-region framework sequences. J Immunol. Apr. 1, 1993;150(7):2844-57.

Smith et al., Comparison of biosequences, Adv. Appl. Math. 1981; 2:482-489.

Spicer et al., CT141 Phase 1 trial of MOv18, a first in class IgE antibody therapy for cancer. Session VPO.CT01—Virtual Meeting I: Phase I Clinical Trials. Apr. 27, 2020, 1-2.

Stewart et al., Solid Phase Peptide Synthesis, 2nd ed., Pierce Chem. Co., Rockford, Ill., 1984. TOC only. 8 pages.

Tiller et al., Efficient generation of monoclonal antibodies from single human B cells by single cell RT-PCR and expression vector cloning. J Immunol Methods. Jan. 1, 2008;329(1-2):112-24.

Vercelli et al., The B-cell binding site on human immunoglobulin E. Nature. Apr. 20, 1989;338(6217):649-51.

Verhoeyen et al., Reshaping human antibodies: grafting an antilysozyme activity. Science. Mar. 25, 1988;239(4847):1534-6.

Wang et al., Potential aggregation prone regions in biotherapeutics: A survey of commercial monoclonal antibodies. MAbs. May-Jun. 2009;1(3):254-67.

Ward et al., Binding activities of a repertoire of single immunoglobulin variable domains secreted from *Escherichia coli*. Nature. Oct. 12, 1989;341(6242):544-6.

Weiner et al., Monoclonal antibodies: versatile platforms for cancer immunotherapy. Nat Rev Immunol. May 2010;10(5):317-27.

Wrammert et al., Rapid cloning of high-affinity human monoclonal antibodies against influenza virus. Nature. May 29, 2008;453(7195):667-71.

Yang et al., The significance of the change pattern of serum CA125 level for judging prognosis and diagnosing recurrences of epithelial ovarian cancer. J Ovarian Res. Sep. 15, 2016;9(1):57. 8 pages.

Yoshioka et al., Target-selective joint polymerase chain reaction: a robust and rapid method for high-throughput production of recombinant monoclonal antibodies from single cells. BMC Biotechnol. Jul. 21, 2011:11:75. 12 pages.

* cited by examiner

Figure 1 Amino Acid sequence of MOv18 IgE Light (L) Chain
SEQ ID NO:1

DIQMTQTTSSLSASLGDRVTISCRASQDINNFLNWYQQKPDGTVKLLIYYTSRLHSGVP
SRFSGSGSGTDYSLTIINLEQEDIAIYFCQQSSTIPRTFGGGTKLEIKRTVAAPSVFIF
PPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

Mouse V_L in bold
Human C_L in standard text

Figure 2 Amino Acid sequence of MOv18 IgE Heavy (H) Chain
SEQ ID NO:2

QVQLQQSGAELARPGASVKLSCKASDYIFTNYDITWVKQRPGQGLEWIGEIDPRSGKSYY
NEKFKGKSTLTADKSSSTAYMELRSLTSEDSAVYFCATMYYYGSSPPMDYWGQGTSVTVS
SASTQSPSVFPLTRCCKNIPSNATSVTLGCLATGYFPEPVMVTWDTGSLNGTTMTLPATT
LTLSGHYATISLLTVSGAWAKQMFTCRVAHTPSSTDWVDNKTFSVCSRDFTPPTVKILQS
SCDGGGHFPPTIQLLCLVSGYTPGTINITWLEDGQVMDVDLSTASTTQEGELASTQSELT
LSQKHWLSDRTYTCQVTYQGHTFEDSTKKCADSNPRGVSAYLSRPSPFDLFIRKSPTITC
LVVDLAPSKGTVNLTWSRASGKPVNHSTRKEEKQRNGTLTVTSTLPVGTRDWIEGETYQC
RVTHPHLPRALMRSTTKTSGPRAAPEVYAFATPEWPGSRDKRTLACLIQNFMPEDISVQW
LHNEVQLPDARHSTTQPRKTKGSGFFVFSRLEVTRAEWEQKDEFICRAVHEAASPSQTVQ
RAVSVNPGK

Mouse V_H in bold
Human C_H in standard text

**Figure 3 Amino Acid sequence of MOv18 IgE Light Chain Variable Domain
SEQ ID NO:3**

DIQMTQTTSSLSASLGDRVTISCRASQDINNFLNWYQQKPDGTVKLLIYYTSRLHSGVP
SRFSGSGSGTDYSLTIINLEQEDIAIYFCQQSSTIPRTFGGGTKLEIK

**Figure 4 Amino Acid sequence of MOv18 IgE Heavy Chain Variable Domain
SEQ ID NO:4**

QVQLQQSGAELARPGASVKLSCKASDYIFTNYDITWVKQRPGQGLEWIGEIDPRSGKSYY
NEKFKGKSTLTADKSSSTAYMELRSLTSEDSAVYFCATMYYYGSSPPMDYWGQGTSVTVS
S

Figure 5

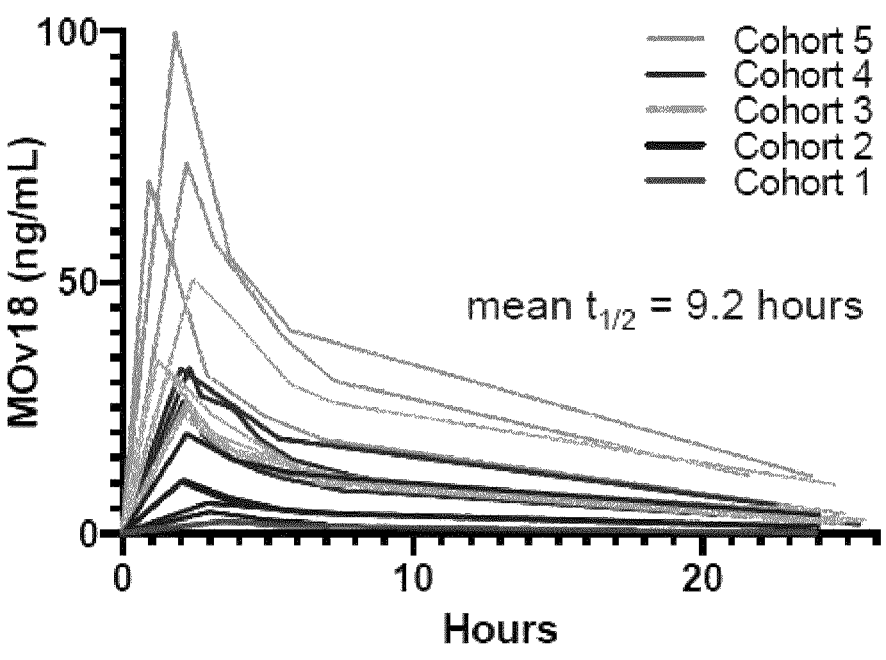

Figure 6

Target Lesions:

Pre Study: LEFT HEMIDIAPHRAGM THICKNESS 21mm; LEFT ILIAC FOSSA DEPOSIT 37mm.
     Total = 58mm End of Cycle 2: LEFT HEMIDIAPHRAGM THICKNESS 18mm; LEFT ILIAC FOSSA DEPOSIT
30mm.          Total 48mm Maintenance Period: LEFT HEMIDIAPHRAGM THICKNESS 18mm; LEFT ILIAC FOSSA DEPOSIT
32mm .          Total 50mm 17% reduction in the sum of the diameter of the target lesions

Non-target lesions:

Pre Study:            Peritoneal disease – present; ascites - present
End of Cycle 2:       Peritoneal disease – present; ascites - absent
Maintenance Period:  Peritoneal disease – present; ascites - absent

*1: dose frequency dropped from once weekly to once every 14 days in weeks 6 - 12*

COMPOSITION COMPRISING AN IgE ANTIBODY

This application is a national phase application under 35 U.S.C. § 371 of PCT International Application No.: PCT/EP2021/060749, filed on Apr. 23, 2021, which claims the benefit of GB Patent Application No. 2006093.5, filed Apr. 24, 2020, the contents of each of which are incorporated by reference herein.

FIELD OF THE INVENTION

The present invention relates to the field of therapeutic antibodies and in particular to dosage regimens and pharmaceutical unit dosage forms for immunoglobulin E (IgE) antibodies. The present invention also relates to methods of treating diseases such as cancer using such IgE antibodies and dosage regimens.

BACKGROUND

Therapeutic antibodies now complement conventional treatments for a number of malignant diseases, but almost all agents currently developed rely on only one of the nine human antibody classes, namely $IgG_1$, the most abundant antibody class in the blood (Weiner L M, Surana R, Wang S (2010) Monoclonal antibodies: versatile platforms for cancer immunotherapy. Nat Rev Immunol 10:317-327). The human immune system naturally deploys nine antibody classes and subclasses (IgM, IgD, IgG1-4, IgAQ1, IgA2 and IgE) to perform immune surveillance and to mediate destruction of pathogens in different anatomical compartments. Yet only IgG (most often IgG1) has been applied in immunotherapy of cancers.

One reason may be that IgG antibodies (particularly IgG1), constitute the largest fraction of circulating antibodies in human blood. The choice of antibody class is also based on pioneering work in the late 1980s, comparing a panel of chimaeric antibodies of the same specificity, each with Fc regions belonging to one of the nine antibody classes and subclasses (Bruggemann M, Williams G T, Bindon C I, Clark M R, Walker M R, Jefferis R, Waldmann H, Neuberger M S (1987) Comparison of the effector functions of human immunoglobulins using a matched set of chimeric antibodies. J Exp Med 166:1351-1361). Antibodies were evaluated for their ability to bind complement and their potency to mediate haemolysis and cytotoxicity of antigen-expressing target cells in the presence of complement. IgG1 in combination with human peripheral blood mononuclear cells (PBMC) was the most effective IgG subclass in complement-dependent cell killing in vitro, while the IgA and IgE antibodies were completely inert.

Subsequent clinical trials with antibodies recognising the B cell marker CD20 supported the inference that IgG1 would be the subclass best suited for immunotherapy of patients with B cell malignancies such as non-Hodgkin's lymphoma (Alduaij W, Illidge T M (2011) The future of anti-CD20 monoclonal antibodies: are we making progress? Blood 117:2993-3001). Since those studies, comparisons of anti-tumour effects by different antibody classes have been confined to IgG and IgM in both murine models and patients with lymphoid malignancies, while IgA has been shown to mediate ADCC in vitro and in vivo in mouse models of lymphoma (Dechant M, Valerius T (2001) IgA antibodies for cancer therapy. Crit Rev Oncol Hematol 39:69-77).

Antibodies of the IgE class play a central role in allergic reactions and have many properties that may be advantageous for cancer therapy. IgE-based active and passive immunotherapeutic approaches have been shown to be effective in both in vitro and in vivo models of cancer, suggesting the potential use of these approaches in humans (Leoh et al., Curr Top Microbiol Immunol. 2015; 388:109-149). Thus IgE therapeutic antibodies may offer enhanced immune surveillance and superior effector cell potency against cancer cells. A mouse/human chimeric IgE antibody (MOv18 IgE), which is specific for the cancer-associated antigen folate receptor $\alpha$, has been demonstrated to have superior antitumor efficacy for IgE compared with an otherwise identical IgG in a syngeneic immunocompetent animal (Gould et al., Eur J Immunol 1999; 29:3527-37; Josephs et al., Cancer Res. 2017 Mar. 1; 77(5): 1127-1141; Karagiannis et al., Cancer Res. 2017 Jun. 1; 77(11): 2779-2783). TNF$\alpha$/MCP-1 signaling was identified as an IgE-mediated mechanism of monocyte and macrophage activation and recruitment to tumors. These findings draw parallels with powerful macrophage-activating functions employed by IgE against parasites, rather than allergic IgE mechanisms. The potential clinical application of IgE-derived drugs in clinical oncology is clear if the antitumor activity of MOv18 IgE in these preclinical experiments can be replicated in patients. In particular, different IgE antibodies with specificity for many other antigens already validated as targets for IgG suggest a wide potential for development of a novel class of antibody therapy.

However the absence of clinical trial data relating to the therapeutic use of IgE antibodies in humans means that appropriate methods of treatment and pharmaceutical compositions involving IgE antibodies are still lacking. In particular, it is not known whether methods and compositions developed for administration of other therapeutic antibody isotypes (e.g. IgG) could be used for IgE antibodies. There is thus a need for methods and compositions, especially unit dosage forms and dosage regimens, that are suitable for IgE antibodies and that are safe and effective in humans.

SUMMARY OF THE INVENTION

Accordingly, in one aspect the present invention provides a pharmaceutical unit dosage composition comprising an antibody of isotype immunoglobulin E (IgE), wherein the composition comprises less than 50 mg of the IgE antibody.

In particular embodiments, the composition comprises less than 30 mg, less than 25 mg, less than 10 mg, less than 5 mg, less than 3 mg or less than 1 mg of the IgE antibody. For instance, the composition may comprise 10 µg to 50 mg, 70 µg to 30 mg, 70 µg to 3 mg, 500 µg to 1 mg or about 700 µg of the IgE antibody.

In one embodiment, the composition is in the form of a liquid. For instance, the composition may comprise an aqueous solution having a concentration of 0.1 mg/ml to 10 mg/ml, 0.5 mg/ml to 2 mg/ml or about 1 mg/ml of the IgE antibody.

In one embodiment, the composition further comprises one or more pharmaceutically acceptable excipients, e.g. sodium citrate, L-arginine, sucrose, polysorbate 20 and/or sodium chloride. Preferably the composition is suitable for intravenous injection, e.g. at a maximum total dose of up to 50 mg/week, 25 mg/week, 10 mg/week, 3 mg/week or 1 mg/week.

In another embodiment, the antibody is an anti-folate receptor $\alpha$ (FR$\alpha$) antibody. Preferably the antibody is a MOv18 IgE antibody. For instance the antibody may comprise a light chain variable domain amino acid sequence as defined in SEQ ID NO:3 and/or a heavy chain variable domain amino acid sequence as defined in SEQ ID NO:4. Most preferably the antibody comprises a light chain amino acid sequence as defined in SEQ ID NO:1 and/or a heavy chain amino acid sequence as defined in SEQ ID NO:2.

In further embodiments, the compositions are used in the treatment of cancer. Thus in a further aspect, the present invention provides a method for treating and/or delaying progression of cancer in a subject in need thereof, comprising a step of administering a pharmaceutical unit dosage composition as defined above to the subject.

The compositions may be administered to a (mammalian) subject suffering from cancer, such as a human subject. Preferably the cancer is ovarian cancer.

In some embodiments, a maximum weekly dose of the IgE antibody administered to the subject is 50 mg, 25 mg, 10 mg, 3 mg or 1 mg. For instance, the weekly dose of the IgE antibody may be 10 µg to 50 mg, 70 µg to 30 mg, 70 µg to 3 mg, 500 µg to 1 mg or about 700 µg.

In one embodiment, the IgE antibody is administered to the subject once a week or once every two weeks, e.g. for up to 12 weeks. In one embodiment, the IgE antibody is administered to the subject (i) once a week for 6 weeks; followed by (ii) once every two weeks for 6 weeks.

In further embodiments, the IgE antibody is administered to the subject in a dose per administration of less than 0.7 mg/kg, less than 0.1 mg/kg or less than 0.03 mg/kg, e.g. in a dose of less than 0.7 mg/kg/week, less than 0.1 mg/kg/week, or less than 0.03 mg/kg/week.

BRIEF DESCRIPTION OF THE DRAWINGS

FIG. 1 shows the amino acid sequence of MOv18 IgE Light (L) Chain (SEQ ID NO:1); the mouse VL in shown in bold and the human CL is shown in standard text.

FIG. 2 shows the amino acid sequence of MOv18 IgE Heavy (H) Chain (SEQ ID NO:2); the mouse VH is shown in bold and the human CH is shown in standard text.

FIG. 3 shows the amino acid sequence of MOv18 IgE light chain variable domain (VL) (SEQ ID NO: 3).

FIG. 4 shows the amino acid sequence of MOv18 IgE heavy chain variable domain (VH) (SEQ ID NO:4).

FIG. 5 shows the pharmacokinetics (serum concentration) of MOv18 IgE following intravenous administration of the antibody.

FIG. 6 shows a CT scan image and the results of tumor measurements taken from the CT scan image indicating a reduction in tumor size in an ovarian cancer subject treated with the 700 µg dose level of MOv18 IgE antibody. The tumor (shown in area within oval on each image) is depicted at baseline (left panel) and after 6 weeks of treatment (right panel). The target and non-target lesion dimensions and status in the subject were determined before and after cycles of treatment with the antibody and after the maintenance period.

DETAILED DESCRIPTION OF THE INVENTION

Figure 7:
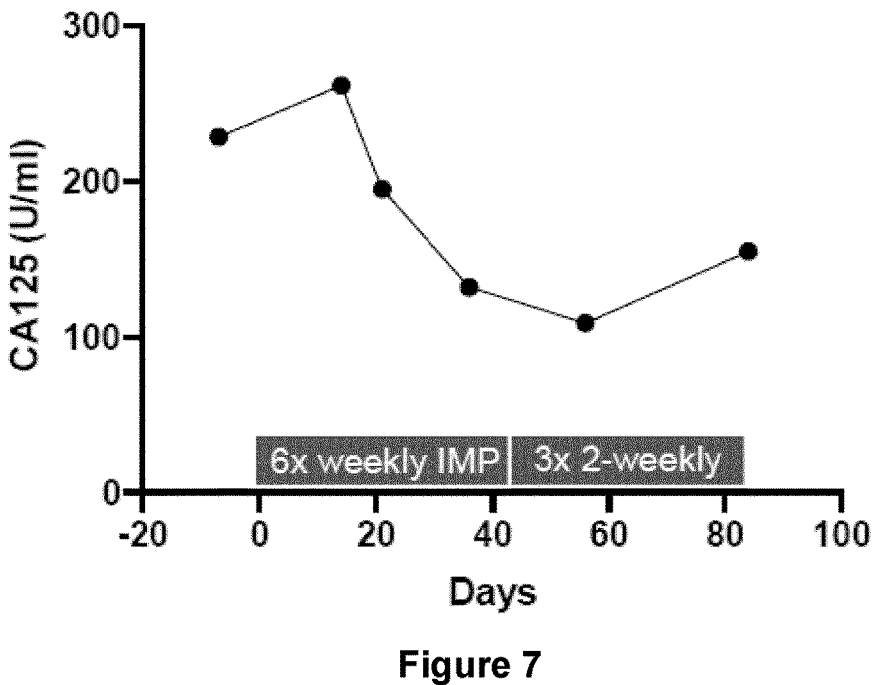
FIG. 7 shows a significant decrease in serum concentration of the ovarian cancer antigen CA125 during treatment of a patient with 6 weekly doses of 700 µg MOv18 IgE antibody, followed by 3 further 700 µg doses of the antibody at 2 week intervals.

It has surprisingly been found that the methods, compositions and dosage forms and regimens that are typically used for IgG antibodies are not necessarily suitable for IgE antibodies. In particular, it has been demonstrated herein that the minimum dose of IgE antibodies required for efficacy (e.g. an anti-tumour effect) can be very much lower than a typical effective dose for IgG antibodies. For instance, as shown in the Example below, an anti-folate receptor $\alpha$ (FR$\alpha$) IgE antibody was found in a Phase I trial to have anti-tumour effects at a unit dose as low as 700 µg (approx. 0.01 mg/kg), which is several orders of magnitude lower than a typical IgG therapeutic antibody dose (e.g. around 150-2000 mg per dose or 2-20 mg/kg). This study was the first trial of a IgE antibody in human subjects, and thus primarily intended to show safety of this new class of therapeutic agent. The demonstration of efficacy was particularly surprising, because the very low doses of IgE tested would be considered unlikely to provoke a significant biological response.

The approved doses and therapeutic windows of some monoclonal (IgG) antibodies approved for the treatment of cancer are shown in Table 1 below (see e.g. Hendrikx et al., Fixed Dosing of Monoclonal Antibodies in Oncology, The Oncologist 2017; 22:1212-1221):

TABLE 1

| Generic name | Approved dose | Therapeutic window[a] |
|---|---|---|
| Bevacizumab | 5 mg/kg; 2 weekly<br>10 mg/kg; 2 weekly<br>15 mg/kg; 3 weekly | 5-15 mg/kg |
| Ipilimumab | 3 mg/kg; 3 weekly | 3-10 mg/kg |
| Nivolumab | 3 mg/kg; 2 weekly | 1-10 mg/kg |
| Obinutuzumab | 1,000 mg per cycle<br>(cycle 2-6) | 1,000-2,000 mg |
| Ofatumumab | 1,000 mg; 4 weekly<br>(untreated CLL)<br>2,000 mg; weekly<br>(refractory CLL) | 1,000-2,000 mg |

TABLE 1-continued

| Generic name | Approved dose | Therapeutic window[a] |
|---|---|---|
| Panitumumab | 6 mg/kg; 2 weekly | 2.5-9 mg/kg |
| Pembrolizumab | 2 mg/kg; 3 weekly | 1-10 mg/kg |
| Pertuzumab | 420 mg; 3 weekly (840 mg loading dose) | 420-1,050 mg |
| Ramucirumab | 8 mg/kg; 2 weekly | 8-10 mg/kg |
| Trastuzumab | 2 mg/kg/week (with an additional 2 mg/kg as loading dose) | 1->8 mg/kg |

[a]The therapeutic window is based on a minimum effective dose at the interval of the approved dose and a maximum tolerated (or tested) dose after single administration.

Accordingly embodiments of the present invention provide the surprising advantage that the IgE antibody can be administered at a very low unit dose compared to IgG antibodies, e.g. less than 50 mg or less than 1 mg/kg (e.g. 500 µg to 10 mg or 0.005 to 0.1 mg/kg). Such low dose compositions are well tolerated, reduce the risk of side effects associated with therapeutic administration of the antibody and require less drug product (thus are relatively inexpensive to produce). The potential efficacy of IgE antibodies at such low doses was a completely unpredictable result, particularly based on the dosage regimens for existing IgG therapeutic antibodies.

This result demonstrates that due to the differences in the pharmacology and pharmacokinetics of IgG and IgE, methods and compositions (such as dosage regimens and unit dosage forms) developed for IgG antibodies are not necessarily transferrable to IgEs. The present inventors therefore developed new dosage regimens and unit dosage forms that are particularly applicable to therapeutic IgE administration, e.g. in the treatment of cancer.

Therapeutic Antibody

Antibodies are polypeptide ligands comprising at least a light chain or heavy chain immunoglobulin variable region which specifically recognizes and specifically binds an epitope of an antigen, such as FRα, or a fragment thereof. Antibodies are typically composed of a heavy and a light chain, each of which has a variable region, termed the variable heavy (VH) region and the variable light (VL) region. Together, the VH region and the VL region are responsible for binding the antigen recognized by the antibody.

Antibodies include intact immunoglobulins and the variants and portions of antibodies well known in the art, provided that such fragments retain at least one function of IgE, e.g. are capable of binding an Fcε receptor. Antibodies also include genetically engineered forms such as chimaeric, humanized (for example, humanized antibodies with murine sequences contained in the variable regions) or human antibodies, heteroconjugate antibodies (such as, bispecific antibodies), e.g. as described in Kuby, J., Immunology, 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are nine main isotypes or classes which determine the functional activity of an antibody molecule: IgA1-2, IgD, IgE, IgG1-4 and IgM, corresponding to the heavy chain types α, δ, ε, γ, and µ. Thus, the type of heavy chain present defines the class of antibody. Distinct heavy chains differ in size and composition; α and γ contain approximately 450 amino acids, while µ and ε have approximately 550 amino acids. The differences in the constant regions of each heavy chain type account for the different effector functions of each antibody isotype, by virtue of their selective binding to particular types of receptor (e.g. Fc receptors). Accordingly, in embodiments of the present invention the antibody preferably comprises an epsilon (ε) heavy chain, i.e. the antibody is of the isotype IgE which binds to Fcε receptors.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., Sequences of Proteins of Immunological Interest, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

Antibodies may have a specific VH region and the VL region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). References to "VH" refer to the variable region of an immunoglobulin heavy chain. References to "VL" refer to the variable region of an immunoglobulin light chain.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimaeric antibody" comprises sequences derived from two different antibodies, which are typically derived from different species. For example, chimaeric antibodies may include human and murine antibody domains, e.g. human constant regions and murine variable regions (e.g. from a murine antibody that specifically binds to a target antigen).

Chimaeric antibodies are typically constructed by fusing variable and constant regions, e.g. by genetic engineering, from light and heavy chain immunoglobulin genes belonging to different species. For example, the variable segments of the genes from a mouse monoclonal antibody can be joined to human constant segments, such as kappa and epsilon. In one example, a therapeutic chimaeric antibody is thus a hybrid protein composed of the variable or antigen-binding domain from a mouse antibody and the constant or effector domain from a human antibody, e.g. an Fc (effector)

domain from a human IgE antibody, although other mammalian species can be used, or the variable region can be produced by molecular techniques. Methods of making chimaeric antibodies are well known in the art, e.g., see U.S. Pat. No. 5,807,715.

A "humanized" antibody is an antibody including human framework regions and one or more CDRs from a non-human (for example a mouse, rat, or synthetic) antibody. The non-human immunoglobulin providing the CDRs is termed a "donor", and the human immunoglobulin providing the framework is teamed an "acceptor". In one embodiment, all the CDRs are from the donor immunoglobulin in a humanized immunoglobulin. The constant regions are typically substantially identical to human immunoglobulin constant regions, i.e., at least about 85-90%, such as about 95% or more identical. Hence, all parts of a humanized immunoglobulin, except the CDRs, are substantially identical to corresponding parts of natural human immunoglobulin sequences.

A humanized antibody typically comprises a humanized immunoglobulin light chain and a humanized immunoglobulin heavy chain. A humanized antibody typically binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions.

Humanized immunoglobulins can be constructed by means of genetic engineering (see for example, U.S. Pat. No. 5,585,089). Typically humanized monoclonal antibodies are produced by transferring donor antibody complementarity determining regions from heavy and light variable chains of a mouse immunoglobulin into a human variable domain, and then substituting human residues in the framework regions of the donor counterparts. The use of antibody components derived from humanized monoclonal antibodies obviates potential problems associated with the immunogenicity of the constant regions of the donor antibody. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Nat'l Acad. Sci. U.S.A. 89:4285, 1992; Sandhu, Crit. Rev. Biotech. 12:437, 1992; and Singer et al., J. Immunol. 150:2844, 1993.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody.

In embodiments of the present invention, the antibodies may be monoclonal or polyclonal antibodies, including chimaeric, humanized or fully human antibodies.

In some embodiments, the antibody binds specifically to folate receptor α (FRα) to form an immune complex. Typically the antibody may comprise an antigen-binding region (e.g. one or more variable regions, or one to 6 CDRs) derived from an antibody which is known to bind. FRα, preferably human FRα, e.g. MOv18 IgE.

FRα, is over-expressed in several solid cancer types (including ovarian and endometrial cancer and mesothelioma). The antigen has been characterised as effectively tumour specific and clinical trials targeting FRα using IgG and IgE antibodies have demonstrated favourable tolerability profiles. The MOv18 IgG and IgE antibodies which bind to FRα and their properties are described, for example, in Coney, L. R., A. Tomassetti, et al. (1991). Cancer Res 51(22): 6125-6132; Gould, H. J., G. A. Mackay, et al. (1999). Eur J Immunol 29(11): 3527-3537; Karagiannis, S. N., Q. Wang, et al. (2003). Eur J Immunol 33(4): 1030-1040.

In one specific embodiment, the antibody comprises a variable region (e.g. a heavy chain variable domain (VH) and/or a light chain variable domain (VL)) or at least one, two, three, four, five or six CDRs (e.g. 3 heavy chain CDRs or 3 light chain CDRs) from MOv18 IgG or IgE, e.g. the CDRs present in SEQ ID NO:4 and/or SEQ ID NO:3, wherein the CDR sequences may be defined according to the method of Kabat, Chothia or IMGT (see e.g. Dondelinger, Front Immunol. 2018; 9:2278 and references cited therein, which are incorporated herein by reference). For instance, CDRs may be defined according to Kabat: see Kabat E A, et al. (U.S.) NI of H. Sequences of Immunoglobulin Chains: Tabulation Analysis of Amino Acid Sequences of Precursors, V-regions, C-regions, J-Chain BP-Microglobulins, 1979; or according to Chothia: see Chothia C, et al, Canonical structures for the hypervariable regions of immunoglobulins, J Mol Biol. 1987 Aug. 20; 196(4): 901-1; or according to IMGT: see Giudicelli V et al., IMGT, the international ImMunoGeneTics database, Nucleic Acids Res. 1997 Jan. 1; 25(1): 206-11 or Lefranc M P, Unique database numbering system for immunogenetic analysis, Immunol Today. 1997 November; 18(11): 509. The amino acid sequences of the VH and VL domains of MOv18 IgE are shown in SEQ ID NO:4 and SEQ ID NO:3, respectively. In another embodiment, the antibody is a chimaeric, humanized or fully human antibody that specifically binds the epitope bound by MOv18 IgE. Most preferably the therapeutic antibody is MOv18 IgE, e.g. the antibody comprises a light chain amino acid sequence as defined in SEQ ID NO:1 and/or a heavy chain amino acid sequence as defined in SEQ ID NO:2.

In another example, the antibody comprises a variable region (e.g. a heavy chain variable domain and/or a light chain variable domain) or at least one, two, three, four, five or six CDRs (e.g. 3 heavy chain CDRs or 3 light chain CDRs) derived from a human B cell clone that recognises an epitope found on e.g. FRα, preferably human FRα.

In one embodiment, the antibody comprises one or more human constant regions, e.g. one or more human heavy chain constant domains (e.g. ε constant domains) and/or a human light chain (e.g. κ or λ) constant domain. An amino acid sequence of a human light (K) chain constant domain is shown in SEQ ID NO:1 (non-bold text). An amino acid sequence of a human heavy chain constant domain is shown in SEQ ID NO:2 (non-bold text). In one embodiment the antibody comprises one or more human framework regions within the VH and/or VL domains.

In one embodiment, the sequence of a humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, U.S. Pat. No. 5,585,089).

Further antibodies against a specific antigen, e.g. FRα, may also be generated by well-established methods, and at least the variable regions or CDRs from such antibodies may be used in the antibodies of the present invention (e.g. the generated antibodies may be used to donate CDR or variable region sequences into IgE acceptor sequences). Methods for synthesizing polypeptides and immunizing a host animal are well known in the art. Typically, the host animal (e.g. a mouse) is inoculated intraperitoneally with an amount of immunogen (e.g. FRα or a polypeptide comprising an immunogenic fragment thereof), and (in the case of monoclonal antibody production) hybridomas prepared from its lymphocytes and immortalized myeloma cells using the general somatic cell hybridization technique of Kohler, B. and Milstein, C. (1975) Nature 25 6:495-497.

Hybridomas that produce suitable antibodies may be grown in vitro or in vivo using known procedures. Monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. If desired, the antibody (monoclonal or polyclonal) of interest may be sequenced and the polynucleotide sequence may then be cloned into a vector for expression or propagation. The sequence encoding the antibody may be maintained in a vector in a host cell and the host cell can then be expanded and frozen for future use.

Phage display technology, for instance as described in U.S. Pat. No. 5,565,332 and other published documents, may be used to select and produce human antibodies and antibody fragments in vitro, from immunoglobulin variable (V) domain gene repertoires from unimmunized donors (e.g. from human subjects, including patients suffering from a relevant disorder). For example, existing antibody phage display libraries may be panned in parallel against a large collection of synthetic polypeptides. According to this technique, antibody V domain genes are cloned in frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus antibody sequences selected using phage display from human libraries may include human CDR or variable region sequences conferring specific binding to a specific antigen such as FRα, which may be used to provide fully human antibodies for use in the present invention.

Methods for deriving heavy and light chain sequences from human B cell and plasma cell clones are also well known in the art and typically performed using polymerase chain reaction (PCR) techniques, examples of the methods are described in: Kuppers R, Methods Mol Biol. 2004; 271:225-38; Yoshioka M et al., BMC Biotechnol. 2011 Jul. 21; 11:75; Scheeren F A et al., PLOS ONE 2011, 6(4): e17189. doi:10.1371/journal.pone.0017189; Wrammert J et al., Nature 2008 453, 667-671; Kurosawa N et al., BMC Biotechnol. 2011 Apr. 13; 11:39; Tiller et al., J Immunol Methods. 2008 Jan. 1; 329(1-2): 112-124. Thus antibody sequences selected using B cell clones may include human CDR or variable region sequences conferring specific binding to e.g. FRα, which may be used to provide fully human antibodies for use in the present invention.

IgE Antibodies

The therapeutic antibody to be administered to the subject is an IgE antibody, i.e. an antibody of the isotype IgE. There are some fundamental structural differences between IgEs and IgGs, and these have functional effects. While IgE shares the same basic molecular architecture as antibodies of other classes, the heavy chain of IgE contains one more domain than the heavy chain of IgG. The Cε3 and Cε4 domains of IgE are homologous in sequence, and similar in structure, to the Cγ2 and Cγ3 domains of IgG, so that it is the Cε2 domains that are the most obvious distinguishing feature of IgE. The Cε2 domain has been found to be folded back against the heavy chain IgE and to make extensive contact with the Cε3 domain. This bent structure of the IgE heavy chain allows it to adopt an open or closed conformation. The unbound IgE dimer has one chain in the open and one chain in the closed conformation. Binding of FcεRI to IgE is biphasic and is thought to involve initial binding to the open Cε chain followed by extensive structural rearrangement to allow binding to the closed Cε chain. The binding between the IgE dimer and the FcεRI occurs with 1:1 stoichiometry despite the presence of two identical Cε-chains. This rearrangement results in a very tight interaction between IgE and FcεRI, and a much greater affinity of IgE for its Fc receptor than found with IgG and FcγRs (McDonnell, J. M., R. Calvert, et al. (2001) Nat Struct Biol 8(5): 437-441).

The antibodies used in the present invention are typically capable of binding to Fcε receptors, e.g. to the FcεRI and/or the FcεRII receptors. Preferably the antibody is at least capable of binding to FcεRI (i.e. the high affinity Fcε receptor) or is at least capable of binding to FcεRII (CD23, the low affinity Fcε receptor). Typically the antibodies are also capable of activating Fcε receptors, e.g. expressed on cells of the immune system, in order to initiate effector functions mediated by IgE.

The epsilon (ε) heavy chain is definitive for IgE antibodies, and comprises an N-terminal variable domain VH, and four constant domains Cε1-Cε4. As with other antibody isotypes, the variable domains confer antigen specificity and the constant domains recruit the isotype-specific effector functions.

IgE differs from the more abundant IgG isotypes, in that it is unable to fix complement and does not bind to the Fc receptors FcγRI, RII and RIII expressed on the surfaces of mononuclear cells, NK cells and neutrophils. However, IgE is capable of very specific interactions with the "high affinity" IgE receptor on a variety of immune cells such as mast cells, basophils, monocytes/macrophages, eosinophils (FcεRI, Ka. $10^{11}$ M$^{-1}$), and with the "low affinity" receptor, Fcε RII (Ka. $10^7$ M$^{-1}$), also known as CD23, expressed on inflammatory and antigen presenting cells (e.g. monocytes/macrophages, platelets, dendritic cells, T and B lymphocytes.

The sites on IgE responsible for these receptor interactions have been mapped to peptide sequences on the Cε chain, and are distinct. The FcεRI site lies in a cleft created by residues between Gln 301 and Arg 376, and includes the junction between the Cε2 and Cε3 domains (Helm, B. et al. (1988) Nature 331, 180183). The FcεRII binding site is located within Cε3 around residue Val 370 (Vercelli, D. et al. (1989) Nature 338, 649-651). A major difference distinguishing the two receptors is that FcεRI binds monomeric Cε, whereas FcεRII will only bind dimerised Cε, i.e. the two Cε chains must be associated. Although IgE is glycosylated in vivo, this is not necessary for its binding to FcεRI and FcεRRII. Binding is in fact marginally stronger in the absence of glycosylation (Vercelli, D. et al. (1989) et. Supra).

Thus binding to Fcε receptors and related effector functions are typically mediated by the heavy chain constant domains of the antibody, in particular by domains which together form the Fc region of the antibody. The antibodies described herein typically comprise at least a portion of an IgE antibody e.g. one or more constant domains derived from an IgE, preferably a human IgE. In particular embodiments, the antibodies comprise one or more domains (derived from IgE) selected from Cε1, Cε2, Cε3 and Cε4. In one embodiment, the antibody comprises at least Cε2 and Cε3, more preferably at least Cε2, Cε3 and Cε4, preferably wherein the domains are derived from a human IgE. In one embodiment, the antibody comprises an epsilon (ε) heavy chain, preferably a human ε heavy chain.

The amino acid sequences of constant domains derived from human IgE are shown in e.g. FIGS. 1 and 2 (SEQ ID NO:s 1 and 2, non-bold text). Nucleotide sequences encoding constant domains derived from human IgE, in particular Cε1, Cε2, Cε3 and Cε4 domains, are also disclosed in e.g. WO 2013/050725. The amino acid sequences of other human and mammalian IgEs and domains thereof, including human Cε1, Cε2, Cε3 and Cε4 domains and human & heavy chain sequences, are known in the art and are available from public-accessible databases. For instance, databases of human immunoglobulin sequences are accessible from the International ImMunoGeneTics Information System (IMGT®) website at www.imgt.org. As one example, the sequences of various human IgE heavy (ε) chain alleles and their individual constant domains (Cε1-4) are accessible at www.imgt.org/IMGT_GENE-DB/GENElect?query=2+ IGHE&species=Homo+sapiens.

Preferred Anti-FRα IgE Antibodies

In one embodiment, the anti-FRα antibody comprises a VH domain comprising at least a portion of the amino acid sequence as defined in SEQ ID NO:4, e.g. comprising at least 20, 30, 50 or 100 amino acids of SEQ ID NO:4 or the full length of SEQ ID NO:4 or one, two or three CDRs present in SEQ ID NO:4 (e.g. defined according to Kabat, Chothia or IMGT).

In one embodiment, the anti-FRα antibody comprises a VL domain comprising at least a portion of the amino acid sequence as defined in SEQ ID NO: 3, e.g. comprising at least 20, 30, 50 or 100 amino acids of SEQ ID NO:3 or the full length of SEQ ID NO:3 or one, two or three CDRs present in SEQ ID NO:3 (e.g. defined according to Kabat, Chothia or IMGT).

In general, functional fragments of the sequences defined above may be used in the present invention. Functional fragments may be of any length as specified above (e.g. at least 50, 100, 300 or 500 nucleotides, or at least 50, 100, 200 or 300 amino acids), provided that the fragment retains the required activity when present in the antibody (e.g. specific binding to FRα and/or a Fcε receptor).

Variants of the above amino acid and nucleotide sequences may also be used in the present invention, provided that the resulting antibody binds an Fcε receptor. Typically such variants have a high degree of sequence identity with one of the sequences specified above.

The similarity between amino acid or nucleotide sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of the amino acid or nucleotide sequence will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the antibody (e.g. anti-FRα antibody or a domain thereof, e.g. a VL, VH, CL or CH domain) typically have at least about 75%, for example at least about 80%, 90%, 95%, 96%, 97%, 98% or 99% sequence identity with the original sequence (e.g. a sequence defined above), for example counted over the full length alignment with the amino acid sequence of the antibody or domain thereof using the NCBI Blast 2.0, gapped blastp set to default parameters. For comparisons of amino acid sequences of greater than about 30 amino acids, the Blast 2 sequences function is employed using the default BLO-SUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Typically variants may contain one or more conservative amino acid substitutions compared to the original amino acid or nucleic acid sequence. Conservative substitutions are those substitutions that do not substantially affect or decrease the affinity of an antibody to the target antigen (e.g. FRα) and/or Fcε receptors. For example, a human antibody that specifically binds FRα may include up to 1, up to 2, up to 5, up to 10, or up to 15 conservative substitutions compared to the original sequence (e.g. as defined above) and retain specific binding to the FRα polypeptide. The term conservative variation also includes the use of a substituted amino acid in place of an unsubstituted parent amino acid, provided that antibody specifically binds the target antigen (e.g. FRα). Non-conservative substitutions are those that reduce an activity or binding to the target antigen (e.g. FRα) and/or Fcε receptors.

Functionally similar amino acids which may be exchanged by way of conservative substitution are well known to one of ordinary skill in the art. The following six groups are examples of amino acids that are considered to be conservative substitutions for one another: 1) Alanine (A), Serine(S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Further IgE Antibodies

As described above, in preferred embodiments the IgE antibody binds to FRα. In further embodiments, the IgE antibodies used herein may bind specifically (i.e. via their variable domains or the complementarity determining regions (CDRs) thereof) to one or more further target antigens useful in treating cancer, i.e. to a target antigen other than FRα. For instance, the IgE antibodies may bind ticularly against cancer cells expressing such an antigen. For example, the IgE antibodies may bind specifically e.g. to EGF-R (epidermal growth factor receptor), VEGF (vascular endothelial growth factor) or erbB2 receptor (Her2/neu). One example of an antibody comprising variable domains that bind selectively to Her2/neu is trastuzumab (Herceptin).

In some embodiments, one or more of the variable domains and/or one or more of the CDRs, preferably at least three CDRs, or more preferably all six CDRs may be derived from one or more of the following antibodies: alemtuzumab (SEQ ID NOs: 27-32), atezolizumab (SEQ ID NOs: 33-38), avelumab (SEQ ID NOs: 39-45), bevacizumab (SEQ ID NOs: 46-51), blinatumomab, brentuximab, cemiplimab, certolizumab (SEQ ID NOs: 52-57), cetuximab (SEQ ID NOs: 58-63), denosumab, durvalumab (SEQ ID NOs: 64-69), efalizumab (SEQ ID NOs: 70-75), iplimumab, nivolumab, obinutuzumab, ofatumumab, omalizumab (SEQ ID NOs: 76-81), panitumumab (SEQ ID NOs: 82-87), pembrolizumab, pertuzumab (SEQ ID NOs: 88-93), rituximab (SEQ ID NOs: 94-99), or trastuzumab (SEQ ID NOs: 100-105).

In such embodiments, the variable domains of the antibody may comprise one or more of the CDRs, preferably at least three CDRs, or more preferably all six of the CDR sequences from one of the antibodies listed in Table 2.

TABLE 1

Estimated CDR Amino Acid Sequences for Examples of Antibodies used in Cancer Therapy

| Antibody | CDR H1 | CDRH2 | CDRH3 | CDR L1 | CDR L2 | CDR L3 | Notes |
|---|---|---|---|---|---|---|---|
| Alemtuzumab | GFTF....TDFY (27) | IRDKAKGYTT (28) | AREGHT....AAP FDY (29) | QNI......DKY (30) | NT.......N (31) | LQHIS.... RPRT (32) | 1 A |
| Atezolizumab | DSWIH (33) | WISPYGGSTY (34) | RHWPGGF (35) | DVST.AVA (36) | SASFLY (37) | QQYL.YHPAT2 (38) | B |
| Avelumab | SYIMM (39) | SIYPSGGITF (40) | .IKLFT..VTTV (41) | VGGYNYVS (42) | DVSNRP (43) | SSYTSSSTRV2 (45) | B |
| Bevacizumab | GYTF...TNYG (46) | INTY..TGEP (47) | AKYPHYYGSS HWYFDV (48) | QDISNY (49) | FTS (50) | QQYSTVPWT (51) | 1 A |
| Certolizumab | GYVFT.DYGMN (52) | GWI.NTYIGEPI YADSVK.G (53) | AR..G.YRSYAM DY (54) | KASQNV....GTN VA (55) | SASFLY (56) | QQYNIYPL (57) | 3 A |
| Cetuximab | GFSL....TNYG (58) | IWSG...GNT (59) | ARALTYY...DY EFAY (60) | QSI......GTN (61) | YA.......S (62) | QQNNN.... WPTT (63) | 1 A |
| Durvalumab | RYWMS (64) | NIKQDGSEKY (65) | EGGWFG..ELAF (66) | RVSSSYLA (67) | DASSRA (68) | QQYG.SLPWT2 (69) | B |
| Efalizumab | GYSFT.GHWMN (70) | GIMIHPSDSETR YNQKFKDI (71) | ARIGIYFYGTT YFDYI (72) | RASKTI.....SK YLA (73) | SGSTLQ (74) | QQHNEYPL (75) | 3 A |
| Omalizumab | GYSITSGYSWN (76) | ASI..TYDGSTNY ADSVK.G (77) | ARGSHYF..GH WHFAV (78) | RASQSV.DYDGD SYMN (79) | AASYLE (80) | QQSHEDPY (81) | 3 A |
| Panitumumab | GGSVS..SGDYY (82) | IYYS...GNT (83) | VRDRVT.....GA FDI (84) | QDI......SNY (85) | DA.......S (86) | QHFDH.... LPLA (87) | 1 A |
| Pertuzumab | GFTF....TDYT (88) | VNPN..SGGS (89) | ARNLGP....SFY FDY (90) | QDV.....SIG (91) | SA.......S (92) | QQYYI.... YPYT (93) | 1 A |
| Rituximab | GYTF..TSYN (94) | IYPG..NGDT (95) | ARSTYYG..GD WFNV (96) | SSV.......SY (97) | AT.......S (98) | QQWTS.... NPPT (99) | 1 A |
| Trastuzumab | GFNI....KDTY (100) | IYPT..NGYT (101) | SRWGGDG...FY AMDY (102) | QDV......NTA (103) | SA.......S (104) | QQHYT.... TPPT (105) | 1 A | specifically to one or more further cancer antigens (i.e. antigens expressed selectively or overexpressed on cancer cells). Preferably the IgE antibodies are capable of inducing cytotoxicity (e.g. ADCC) and/or phagocytosis (ADCP), par- In Table 2, numbers indicated in brackets are the corresponding SEQ ID NOs. Dots indicate sequence alignment gaps according to the IMGT and Kabat numbering systems. Letters indicate the method used to predict the CDR sequence. A—IMGT, B—Kabat. 1—Magdelaine-Beuzelin et al. (2007) Structure-function relationships of the variable domains of monoclonal antibodies approved for cancer treatment. Critical Reviews in Oncology/Hematology, 64:210-225. 2—Lee et al. (2017). Molecular mechanism of PD-1/PD-L1 blockade via anti-PD-L1 antibodies atezolizumab and durvalumab. Scientific Reports, 7:5532.3—Ling et al. (2018) Effect of VH-VL Families in Pertuzumab and Trastuzumab Recombinant Production, Her2 and FcγIIA Binding. Frontiers in Immunology, 9:469.

In alternative embodiments, one or more of the variable domains and/or one or more CDRs, preferably at least three CDRs, or more preferably all six CDRs, may be derived from one or more of the following antibodies: abciximab, adalimumab (SEQ ID NOs: 106-111), aducanumab, aducanumab, alefacept, alirocumab, anifrolumab, balstilimab, basiliximab (SEQ ID NOs: 112-117), belimumab (SEQ ID NOs: 118-123), benralizumab, bezlotoxumab, brodalumab, brolucizumab, burosumab, cankinumab, caplacizumab, crizanlizumab, daclizumab (SEQ ID NOs: 124-129), daratumumab, dinutuximab, dostarlimab, duplilumab, eclizumab, elotuzumab, emapalumab, emicizumab, epitinezumab, erenumab, etrolizumab, evinacumab, evolocumab, fremanezumab, galcanezumab, golimumab, guselkumab, ibalizumab, idarucizumab, inebilizumab, infliximab (SEQ ID NOs: 130-135), isatuximab, ixekizumab, lanadelumab, leronlimab, margetuximab, mepolizumab, mogamulizumab, muromonab, narsoplimab, natalizumab (SEQ ID NOs: 136-141), naxitamab, necitumumab, obiltoxaximab, ocrelizumab, omburtamab, palivizumab (SEQ ID NOs: 5-10), ramucirumab, ranibizumab (SEQ ID NOs: 11-16), reslizumab, risankizumab, romosozumab, sarilumab, satralizumab, secukinumab, spartalizumab, sutimlimab, tafasitamab, tanezumab, teplizumab, teprotumumab, tildrakizumab, toclizumab, toropalimab, ustekinumab, vedolizumab or zalifrelimab.

In such embodiments, the variable domains of the antibody may comprise one or more of the CDRs, preferably at least three CDRs, or more preferably all six of the CDR sequences from one of the antibodies listed in Table 3.

In Table 3, numbers indicated in brackets are the corresponding SEQ ID NOs. Dots indicate sequence alignment gaps according to the IMGT and Kabat numbering systems. Letters indicate the method used to predict the CDR sequence. A—IMGT, B—Kabat. 1—Schröter et al. (2014) A generic approach to engineer antibody pH-switches using combinatorial histidine scanning libraries and yeast display. MAbs, 7(1): 138-151. 2—Wang et al. (2009). Potential aggregation prone regions in biotherapeutics. A survey of commercial monoclonal antibodies. MAbs, 1(3): 254-267. 3—WO 2015/173782 A1. 4—Lim et al. (2018). Structural Biology of the TNFα Antagonists Used in the Treatment of Rheumatoid Arthritis. International Journal of Molecular Sciences, 19(3): pii E768.

In other embodiments, one or more of the variable domains and/or one or more of the CDR sequences, preferably at least three CDRs, or more preferably all six CDRs, may be derived from an anti-HMW-MAA antibody. In one embodiment, one or more of the variable domains and/or one or more of the CDR sequences, preferably at least three CDRs, or more preferably all six CDRs may be derived from the anti-HMW-MAA antibody described in WO 2013/050725 (SEQ ID NOs: 23 and 25 for the variable domain and SEQ ID NOs: 17-22 for CDR). HMW-MAA refers to high molecular weight-melanoma associated antigen, also known as chondroitin sulfate proteoglycan 4 (CSPG4) or melanoma chondroitin sulfate proteoglycan (MCSP)—see e.g. Uniprot Q6UVK1.

In such embodiments, the variable domains of the antibody may comprise one or more of the CDR sequences, preferably at least three CDRs, or more preferably all six of the CDR sequences defined in Table 4. In other embodiments, one or more of the variable domains of the antibody comprises one or more of the variable domain sequences listed in Table 4.

TABLE 3

| Estimated CDR Amino Acid Sequences for Example Therapeutic Antibodies | | | | | | | |
|---|---|---|---|---|---|---|---|
| Antibody | CDR H1 | CDRH2 | CDRH3 | CDR L1 | CDR L2 | CDR L3 | Notes |
| Adalimumab | DYAMH (106) | AITWNSGHIDYADSVEG (107) | VSYLSTASSLDY (108) | RASQGIRNYLA (109) | AASTLQS (110) | QRYNRAPYT (111) | 1 A |
| Basiliximab | GYSFTR.. YWMH (112) | AIYPGNSD..TSYNQKFEG (113) | DYGY.....YFDF (114) | SASSSRSY...... MQ (115) | DTSKLAS (116) | HQRSS..YT (117) | 2 |
| Belimumab | GGTFNNNAIN (118) | GIIPMFGTAKYSQNFQG (119) | SRDLLLFPHHALSP (120) | QGDSLRSYYAS (121) | GKNNRPS (122) | SSRDSSGNHWV (123) | 3B |
| Daclizumab | GYTFTS.. YRMH (124) | YINPSTGY..TEYNQKFKD (125) | GG......GVFDY (126) | SASSSISY...... MH (127) | TTSNLAS (128) | HQRSTYPLT (129) | 2 |
| Infliximab | IFSNHW (130) | RSKSINSATH (131) | N...YYGSTY (132) | FVGSSIH (133) | KYASESM (134) | QSHSW (135) | 4 |
| Natalizumab | GFNIKD.. TYIH (136) | RIDPANGY..TKYDPKFQG (137) | EGYYGNYGVYAMDY (138) | KTSQDINK.... YMA (139) | YTSALQP (140) | LQYDN.LWT (141) | 2 |
| Palivizumab | GFSLSTSGMS VG (5) | DIWWDDK...KDYNPSLKS (6) | SM....ITNWYFDV (7) | KCQLSVGY...... MH (8) | DTSKLAS (9) | FQGSGYPFT (10) | 2 |
| Ranibizumab | GYDFTH.. YGMN (11) | WINTYTGE..PTYAADFKR (12) | YPYYYGTSHWFDV (13) | SASQDISN..... YLN (14) | FTSSLHS (15) | QQYSTVPWT (16) | 2 |

TABLE 4

Estimated Variable Domains and CDR Sequences of an Anti-HMW-MAA
Antibody

| Region | SEQ ID NO. | Amino Acid Sequence |
|---|---|---|
| CDR H1 | 17 | GFTFSNYW |
| CDR H2 | 18 | IRLKSNNFGR |
| CDR H3 | 19 | TSYGNYVGHYFDH |
| CDR L1 | 20 | QNVDTN |
| CDR L2 | 21 | SAS |
| CDR L3 | 22 | QQYNSYPLT |
| Variable Domain (Heavy Chain) | 23 | EQVKLQQSGGGLVQPGGSMKLSCVVSGFTFSNYWM NWVRQSPEKGLEWIAEIRLKSNNFGRYYAESVKGRF TISRDDSKSSAYLQMINLRAEDTGIYYCTSYGNYVGH YFDHWGQGTTVTVSS |
| Alternative Variable Domain (Heavy Chain) | 24 | EVQLVQSGGGLVQPGGSLKLSCAVSGFTFSNYWMN WVRQAPGKGLEWVGEIRLKSNNFGRYYAESVKGRF TISRDDSKNTAYLQMNSLKTEDTAVYYCTSYGNYVG HYFDHWGQGTLVTVSS |
| Variable Domain (Light Chain) | 25 | DIELTQSPKFMSTSVCDRVSVTCKASQNVDTNVAWY QQKPGQSPEPLLFSASYRYTGVPDRFTGSGSGTDFTL TISNVQSEDLAEYFCQQYNSYPLTFGGGTKLEIK |
| Alternative Variable Domain (Light Chain) | 26 | DIQLTQSPSFLSASVGDRVTITCKASQNVDTNVAWYQ QKPGKAPKPLLFSASYRYTGVPSRFSGSGSGTDFTLTI SSLQPEDFATYFCQQYNSYPLTFGGGTKVEIK |

Production of Antibodies and Nucleic Acids

Nucleic acid molecules (also referred to as polynucleotides) encoding the polypeptides provided herein (including, but not limited to antibodies and functional fragments thereof) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies are provided herein.

Nucleic acid sequences encoding the antibodies that specifically bind the target antigen (e.g. FRα), or functional fragments thereof, can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage & Caruthers, Tetra. Letts. 22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding antibodies, or functional fragments thereof, can be prepared by cloning techniques. Examples of appropriate cloning and sequencing techniques, and instructions sufficient to direct persons of skill through many cloning exercises are found see, for example, Molecular Cloning: A Laboratory Manual, 2nd ed., vol. 1-3, ed. Sambrook et al., Cold Spring Harbor Laboratory Press, Cold Spring Harbor, N.Y., 1989); and Current Protocols in Molecular Biology (Ausubel et al., eds 1995 supplement)). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native antibodies can be modified to form the antibodies described herein. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, antibodies are prepared by inserting a cDNA which encodes one or more antibody domains (e.g.

a mouse IgG1 heavy chain variable region which binds human FRα) into a vector which comprises a cDNA encoding one or more further antibody domains (e.g. a human heavy chain ε constant region). The insertion is made so that the antibody domains are read in frame that is in one continuous polypeptide which contains a functional antibody region.

In one embodiment, cDNA encoding a heavy chain constant region is ligated to a heavy chain variable region so that the constant region is located at the carboxyl terminus of the antibody. The heavy chain-variable and/or constant regions can subsequently be ligated to a light chain variable and/or constant region of the antibody using disulfide bonds.

Once the nucleic acids encoding the antibody or functional fragment thereof have been isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including E. coli, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated antibodies and antibody fragments described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For E. coli, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be co-transformed with polynucleotide sequences encoding the antibody, labelled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (e.g., a human FRα-specific IgE antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the antibodies of the present disclosure can also be constructed in whole or in part using standard peptide synthesis well known in the art.

Once expressed, the recombinant antibodies can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the antibodies disclosed herein. See, Buchner et al., Anal. Biochem. 205:263-270, 1992; Pluckthun, Biotechnology 9:545, 1991; Huse et al., Science 246:1275, 1989 and Ward et al., Nature 341:544, 1989.

Often, functional heterologous proteins from E. coli or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9:5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labelled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments.

Methods of forming peptide bonds by activation of a carboxyl terminal end (such as by the use of the coupling reagent N,N'-dicylohexylcarbodimide) are well known in the art.

In one embodiment, the antibodies, nucleic acids, expression vectors, host cells or other biological products are isolated. By "isolated" it is meant that the product has been substantially separated or purified away from other biological components in the environment (such as a cell) in which the component naturally occurs, i.e., other chromosomal and extra-chromosomal DNA and RNA, proteins and organelles. Nucleic acids and antibodies that have been "isolated" include nucleic acids and antibodies purified by standard purification methods. The term also embraces nucleic acids and antibodies prepared by recombinant expression in a host cell as well as chemically synthesized nucleic acids.
Compositions and Therapeutic Methods Compositions are provided herein that include a carrier and one or more therapeutic IgE antibodies, or functional fragments thereof. The compositions can be prepared in unit dosage forms for administration to a subject. The antibody can be formulated for systemic or local (such as intratumour) administration. In one example, the therapeutic IgE antibody is formulated for parenteral administration, such as intravenous administration.

The compositions for administration can include a solution of the antibody (or a functional fragment thereof) dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the antibody and excipients in these formulations can vary, and will be selected primarily based on fluid volumes, viscosities, body weight and the like in accordance with the particular mode of administration selected and the subject's needs. Actual methods for preparing administrable compositions will be known or apparent to those skilled in the art and are described in more detail in such publications as Remington's Pharmaceutical Science, 19th ed., Mack Publishing Company, Easton, Pa. (1995).

In preferred embodiments the compositions are provided as unit dosage forms, e.g. comprising a defined amount of the IgE antibody suitable for administration to a subject in a single dose. The unit dosage forms may be packaged individually, e.g. in single containers, vials, pre-filled syringes or the like. The unit dosage forms may be suitable for immediate administration to the subject (e.g. may comprise a physiologically acceptable concentration of salts) or the unit dosage forms may be provided in concentrated or lyophilized form (e.g. for dilution with sterile saline solution before use).

In embodiments described herein, a typical unit dose of the pharmaceutical composition (e.g. for intravenous administration) comprises less than 50 mg of the IgE antibody. For instance, the composition (i.e. in unit dosage form) may comprise less than 40 mg, 30 mg, 25 mg, 20 mg, 15 mg, 10 mg, 5 mg, 3 mg, or 1 mg of the IgE antibody. The composition may comprise at least 10 µg, 100 µg, 200 µg, 300 µg, 500 µg, 700 µg, 1 mg, 3 mg, 5 mg or 10 mg of the IgE antibody. In preferred embodiments, the composition comprises comprising 10 µg to 50 mg, 70 µg to 30 mg, 300 µg to 50 mg, 300 µg to 30 mg, 300 µg to 3 mg, 500 µg to 50 mg, 500 µg to 30 mg, 500 µg to 10 mg, 500 µg to 3 mg, 700 µg to 50 mg, 700 µg to 30 mg, 700 µg to 10 mg, 700 µg to 3 mg, 500 µg to 5 mg, 500 µg to 1 mg, or about 700 µg of the IgE antibody. In some embodiments, the composition may comprise an amount of the IgE antibody within one or more of the above ranges, but excluding one or more of the following amounts: 1 µg, 5 µg, 10 µg, 50 ug, 100 µg, 500 µg, 1 mg, 2 mg, 4 mg, 5 mg, 10 mg or 15 mg. For instance, the composition may comprise 2 µg to 9 µg, 11 µg to 99 µg, 101 µg to 499 µg, 501 to 999 µg or 2 mg to 9 mg.

The dosage of the IgE antibody administered to the subject may be based on the subject's body weight. Thus the dose of the IgE antibody administered to the subject may be e.g. less than 1 mg/kg. Preferably the IgE antibody may be administered to the subject in a dose (per administration) of e.g. less than 0.7 mg/kg, 0.5 mg/kg, 0.3 mg/kg, 0.1 mg/kg, 0.07 mg/kg, 0.05 mg/kg, 0.03 mg/kg or 0.01 mg/kg. The dose of the IgE antibody administered to the subject may be at least 0.001 mg/kg, 0.003 mg/kg, 0.005 mg/kg, 0.007 mg/kg, 0.01 mg/kg, 0.05 mg/kg or 0.1 mg/kg. In preferred embodiments, the dose of the IgE antibody administered to the subject may be 0.001-1 mg/kg, 0.003-0.7 mg/kg, 0.005-0.5 mg/kg, 0.005-0.1 mg/kg, 0.005-0.05 mg/kg, 0.007-0.03 mg/kg or 0.007-0.15 mg/kg. In some embodiments, the dose of the IgE antibody administered to the subject may be within one or more of the above defined ranges, but excluding one or more of the following dosages: 1 µg/kg, 10 µg/kg, 100 µg/kg or 0.5 mg/kg. For instance, the dose of the IgE antibody may be 2 to 9 µg/kg, 11 to 99 µg/kg, 101 to 499 µg/kg or 0.51 to 0.7 mg/kg.

In embodiments of the present invention, the unit dosages of the IgE antibody described above are at administered at most once a week, e.g. the maximum weekly dose of the IgE antibody is 50 mg, 40 mg, 30 mg, 25 mg, 20 mg, 15 mg, 10 mg, 5 mg, 3 mg, or 1 mg. For instance the weekly dose of the IgE antibody may be 10 µg to 50 mg, 70 µg to 30 mg, 300 µg to 50 mg, 300 µg to 30 mg, 300 µg to 3 mg, 500 µg to 50 mg, 500 µg to 30 mg, 500 µg to 10 mg, 500 µg to 3 mg, 700 µg to 50 mg, 700 µg to 30 mg, 700 µg to 10 mg, 700

μg to 3 mg, 500 μg to 5 mg, 500 μg to 1 mg, or about 700 μg. The weekly dose of the IgE antibody may also be determined according to the subject's body weight, e.g. the IgE antibody may be administered to the subject in a dose of e.g. less than 0.7 mg/kg/week, 0.5 mg/kg/week, 0.3 mg/kg/week, 0.1 mg/kg/week, 0.07 mg/kg/week, 0.05 mg/kg/week, 0.03 mg/kg/week or 0.01 mg/kg/week. In preferred embodiments, the dose of the IgE antibody administered to the subject may be 0.001-1 mg/kg/week, 0.003-0.7 mg/kg/week, 0.005-0.5 mg/kg/week, 0.005-0.1 mg/kg/week, 0.005-0.05 mg/kg/week, 0.007-0.03 mg/kg/week or 0.007-0.15 mg/kg/week. In some embodiments, the dose of the IgE antibody administered to the subject may be within one or more of the above defined ranges, but excluding one or more of the following dosages: 1 μg/kg/day (7 μg/kg/week), 10 μg/kg/day (70 μg/kg/week) or 100 μg/kg/day (0.7 mg/kg/week). For instance, the dose of the IgE antibody may be 2 to 6 μg/kg/week, 8 to 69 μg/kg/week, or 71 to 699 μg/kg/week.

In one embodiment, the pharmaceutical composition is a liquid comprising one or more excipients selected from sodium citrate, L-arginine, sucrose, polysorbate 20 and/or sodium chloride. Preferably the composition has a pH of 6.0 to 8.0, e.g. about 6.5. Preferred concentrations of the excipients include: 0.05 to 0.5 M (e.g. about 0.1 M) sodium citrate; 10 to 50 g/L (e.g. about 30 g/L) L-arginine; 10 to 100 g/L (e.g. about 50 g/L) sucrose; 0.01 to 0.05% w/w (e.g. 0.02% w/w) polysorbate 20. In one embodiment, the IgE antibody is present in such a formulation at a concentration of about 0.1 mg/ml to 10 mg/ml or 0.5 mg/ml to 2 mg/ml, e.g. about 1 mg/ml. In some embodiments, such a composition may be formulated as a unit dosage form e.g. in a volume of about 1 ml of solution comprising about 1 mg of the IgE antibody, for instance in a 2 ml type I glass vial. The composition may be diluted with sterile saline (0.9% w/v) before administration to the subject, e.g. in an amount of 1 ml of the composition in 250 ml of saline.

Antibodies may be provided in lyophilized form and rehydrated with sterile water before administration, although they are also provided in sterile solutions of known concentration. The antibody solution is then added to an infusion bag containing 0.9% sodium chloride, USP, and administered to the subject. Considerable experience is available in the art in the administration of antibody drugs, which have been marketed in the U.S. since the approval of RITUXAN (Registered trademark) in 1997. Antibodies can be administered by slow infusion, rather than in an intravenous push or bolus. In one example, a higher loading dose is administered, with subsequent, maintenance doses being administered at a lower level. For example, an initial loading dose may be infused over a period of some 90 minutes, followed by weekly maintenance doses for 4-8 weeks infused over a 30 minute period if the previous dose was well tolerated.

The antibody (or functional fragment thereof) can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. In some embodiments, the antibodies are administered to a subject to inhibit or prevent the development of metastasis, or to decrease the size or number of metastases, such as micrometastases, for example micrometastases to the regional lymph nodes (Goto et al., Clin. Cancer Res. 14(11): 3401-3407, 2008).

Thus in some embodiments, the IgE antibody is used to treat cancer and/or to delay or prevent the progression of cancer. By "delay or prevent the progression" of cancer it is meant that, for example, the cancer is at least stable for a period of time after administration of the antibody, e.g. for at least 6 weeks, at least 12 weeks, at least 6 months or at least 12 months. "Stable" disease may be defined e.g. as a change in the RECIST score of less than 20%.

RECIST (Response Evaluation Criteria in Solid Tumours) evaluation is a simple method for determining whether a patient's disease has improved, stayed about the same, or worsened following treatment with a cancer therapeutic, and is commonly used in clinical trials of anticancer agents. The RECIST criteria are specified e.g. in Eisenhauer et al., New response evaluation criteria in solid tumours: Revised RECIST guideline (version 1.1), European Journal Of Cancer 45 (2009) 228-247. RECIST defines Progressive Disease (PD) as at least a 20% increase in the sum of diameters of target lesions, taking as reference the smallest sum on study. Stable disease is defined as neither sufficient shrinkage to qualify for Partial Response (at least a 30% decrease in the sum of diameters of target lesions), nor sufficient increase to qualify for PD, i.e. an increase of <20% is defined as stable disease.

It will be appreciated that in this context "at least stable" includes an increase or decrease in the RECIST score of less than 20%. Thus the antibody may delay or prevent progression of the disease (e.g. delay or prevent appearance of one or more signs or symptoms or cancer, and/or inhibit the growth of cancer cells and/or prevent or reduce metastases), or ameliorate or promote remission of the disease (e.g. reduce or inhibit one or more sign or symptom of cancer, and/or kill cancer cells).

Suitable subjects may include those diagnosed with cancer, e.g. a cancer that expresses FRα, such as, but not limited to, skin cancer (e.g. melanoma), lung cancer, prostate cancer, squamous cell carcinoma (such as head and neck squamous cell carcinoma), breast cancer (including, but not limited to basal breast carcinoma, ductal carcinoma and lobular breast carcinoma), leukemia (such as acute myelogenous leukemia and 11g23-positive acute leukemia), lymphoma, a neural crest tumour (such as an astrocytoma, glioma or neuroblastoma), ovarian cancer, colon cancer, stomach cancer, pancreatic cancer, bone cancer (such as a chordoma), glioma or a sarcoma (such as chondrosarcoma). Preferably the antibody is administered to treat a solid tumour.

A therapeutically effective amount of antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

The invention will now be further described by way of example only, with reference to the following non-limiting embodiments.

Example

Chimeric MOv18 IgE (MOv18 IgE)

Chimeric MOv18 IgE (MOv18 IgE) is an anti-folate receptor α (FRα) monoclonal antibody (mAb) of the IgE class. This antibody has been shown to mediate potent antibody-dependent cell-mediated cytotoxicity (ADCC) and antibody-dependent cellmediated phagocytosis (ADCP) against FRα expressing tumour cell lines in vitro and FRα expressing tumour xenografts in vivo. The target antigen, FRα, is over-expressed in several solid cancer types (including ovarian and endometrial cancer and mesothelioma). The antigen has been characterised as effectively tumour specific and clinical trials targeting FRα using IgG antibodies, including trials of chimeric MOv18 IgG1 (MOv18 IgG1), have demonstrated favourable tolerability profiles. MOv18 IgE is thought to have a mechanism of action involving binding to blood effector cells including monocytes, basophils and eosinophils. These IgE carrying cells enter tissues and, upon encountering FRα expressing cells, produce an IgE mediated immune response against the tumour. The MOv18 IgG and IgE antibodies and their properties are described, for example, in Coney, L. R., A. Tomassetti, et al. (1991). "Cloning of a tumor-associated antigen: MOv18 and MOv19 antibodies recognize a folate-binding protein." Cancer Res 51(22): 6125-6132; Gould, H. J., G. A. Mackay, et al. (1999). "Comparison of IgE and IgG antibody-dependent cytotoxicity in vitro and in a SCID mouse xenograft model of ovarian carcinoma." Eur J Immunol 29(11): 3527-3537; Karagiannis, S. N., Q. Wang, et al. (2003). "Activity of human monocytes in IgE antibody dependent surveillance and killing of ovarian tumor cells." Eur J Immunol 33(4): 1030-1040.

Drug Formulation and Administration

MOv18 IgE is a 168 kDa protein having light and heavy chain amino acid sequences as shown in FIGS. 1 (SEQ ID NO:1) and 2 (SEQ ID NO:2). The MOv18 IgE drug product is supplied as a sterile, pyrogen-free and particle-free solution containing 1 mg/mL MOv18 IgE at pH 6.5 as a 1.0 mL fill in a 2 mL vial for dilution prior to infusion. Each vial of MOv18 IgE also contains the excipients 0.1 M sodium citrate, 30 g/L L-arginine 50 g/L sucrose, 0.02% polysorbate 20 in water for injection.

MOv18 IgE is administered by intravenous (IV) infusion after dilution with 0.9% (w/v) saline. In addition, subjects received intradermal [ID] administration of MOv18 IgE (plus histamine and saline controls), prior to every IV administration, to evaluate the risk of anaphylaxis. Alternatively, skin prick testing was used to evaluate anaphylaxis risk. Patients only proceeded to IV administration of MOv18 IgE in the absence of a cutaneous reaction to the antibody.

Prior to administration of the therapeutic antibody, blood samples were obtained from the subjects and subjected to a basophil activation test in the presence of the MOv18 IgE (Flow CAST®, Bühlmann Laboratories AG, Schönenbuch, Switzerland).

Study Design

MOv18 IgE was tested in open label, Phase I multiple ascending dose escalation trial in FRα positive solid tumours. 24 patients with advanced solid tumours expressing FRα were entered into the study. Eligible subjects had adequate organ function, no history of severe allergy and an absence of concomitant medications or comorbidities that could increase risk in the event of anaphylaxis.

Patients received MOv18 IgE once weekly as an IV infusion for a total of six doses, starting at a flat dose of 70 μg. Dose escalation was carried out through defined dose levels (including 70 μg, 250 ug, 500 μg, 700 μg, 1.5 mg and 3 mg) up to a maximum dose of 50 mg. Three weeks of treatment were considered as one cycle during this phase. Patients in any cohort who appeared to be benefitting from MOv18 IgE were given up to three further doses of MOv18 IgE at fortnightly intervals continuing at the same dose level (unless dose-limiting toxicity was encountered or the patient developed progressive disease). This additional period was considered a maintenance phase.

Initially, patients were enrolled in single patient cohorts (Cohorts 1 to 4; 70 to 700 μg doses of MOv18 IgE), as the planned doses are very low and were considered unlikely to provoke a significant biological response. For Cohorts 5 to 10 (1.5 to 50 mg doses of MOv18 IgE), three patients were enrolled per cohort, with an additional three patients added to a cohort if needed for toxicity. Cohorts were expanded up to six patients to further explore the safety and efficacy of MOv18 IgE. No further dose escalation was carried after Cohort 10 (i.e., 50 mg was the top dose evaluated).

Results

In an initial phase of the study, 10 patients had received MOv18 IgE with two patients treated at the 500 μg dose level. Anti-drug antibodies were detected in 3/21 evaluable patients (ADA detected in 2 patients, plus one patient with suspected ADA) at 6 weeks and/or at off study follow up (>8 weeks). One of the patients treated at the 500 μg dose level experienced a grade 3 anaphylactic episode shortly after receiving MOv18 IgE. The patient responded to standard anaphylaxis treatment as per protocol and recovered fully.

The pharmacokinetics of MOv18 IgE (serum concentration) following intravenous administration for particular dose cohorts of subjects are shown in FIG. 5. Cohort 1: 70 μg; Cohort 2: 250 μg; Cohort 3: 500 μg; Cohort 4: 700 μg; Cohort 5: 1.5 mg.

FIGS. 6 and 7 show that administration of MOv18 IgE antibody at a unit dose of 700 μg resulted in anti-tumor effects. FIG. 6 shows the results of tumor measurements taken from a CT scan image showing a reduction in tumor size in an ovarian cancer subject treated with the 700 μg dose level of MOv18 IgE antibody. FIG. 7 shows a significant decrease in serum concentration of the ovarian cancer antigen CA125 during treatment of a patient with 6 weekly doses of 700 μg MOv18 IgE antibody, followed by 3 further 700 μg doses of the antibody at 2 week intervals. A reduction in CA125 during ovarian cancer treatment has been demonstrated to be associated with positive treatment outcomes (see e.g. Yang, Z., Zhao, B. & Li, L. The significance of the change pattern of serum CA125 level for judging prognosis and diagnosing recurrences of epithelial ovarian cancer. J Ovarian Res 9, 57 (2016)). The decrease in CA125 levels shown in FIG. 7 is above the threshold for defining a response to chemotherapy in ovarian cancer according to the Gynecologic Oncology Group (GOG) criteria (see e.g. Rustin et al. Defining response of ovarian carcinoma to initial chemotherapy according to serum CA 125, Journal of Clinical Oncology 1996 14:5, 1545-1551).

Figure 8:
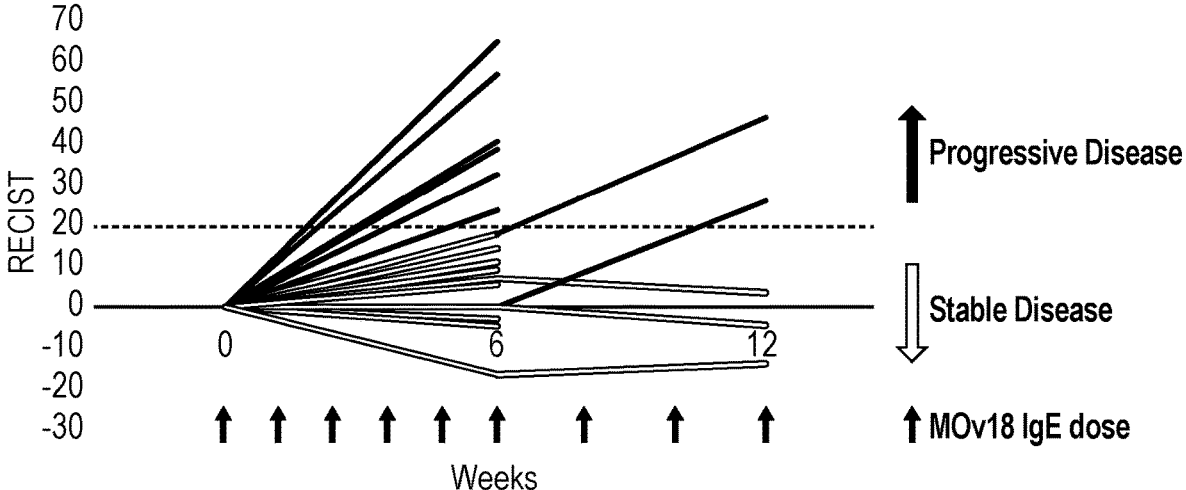
FIG. 8 shows a plot of the change in RECIST (Response Evaluation Criteria in Solid Tumours) scores in individual ovarian cancer subjects treated with a MOv18 IgE antibody. Each line represents the percentage change in RECIST scores in individual patients from the start of treatment, (i.e. after 6 weeks of treatment and after 12 weeks of treatment). A RECIST score that increases or decreases by less than 20% is indicative of stable disease.
Figure 9:
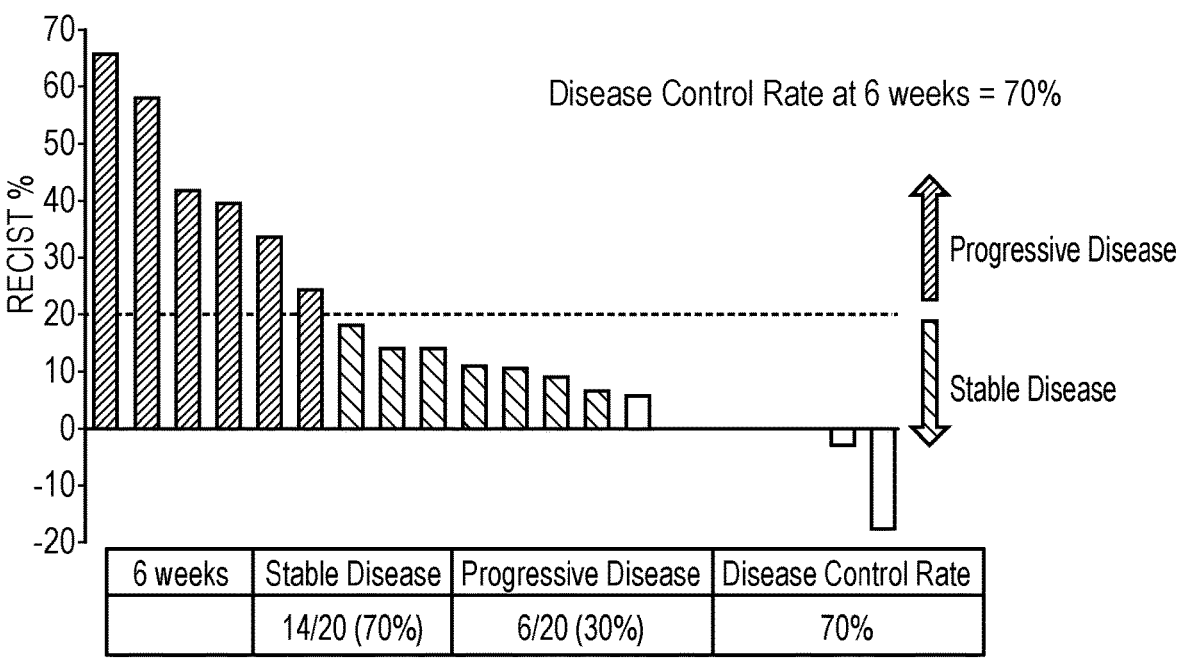
FIG. 9 shows a waterfall plot of the change in RECIST (Response Evaluation Criteria in Solid Tumours) scores in individual ovarian cancer subjects after 6 weeks of treatment with a MOv18 IgE antibody. Each vertical bar represents the change in RECIST score in an individual subject at 6 weeks. 20 subjects in total were treated. Where no vertical bar is shown, this indicates no change in the RECIST score in the subject after 6 weeks (this occurred in four subjects, indicated by the gap between vertical bars along the x-axis).
Figure 10:
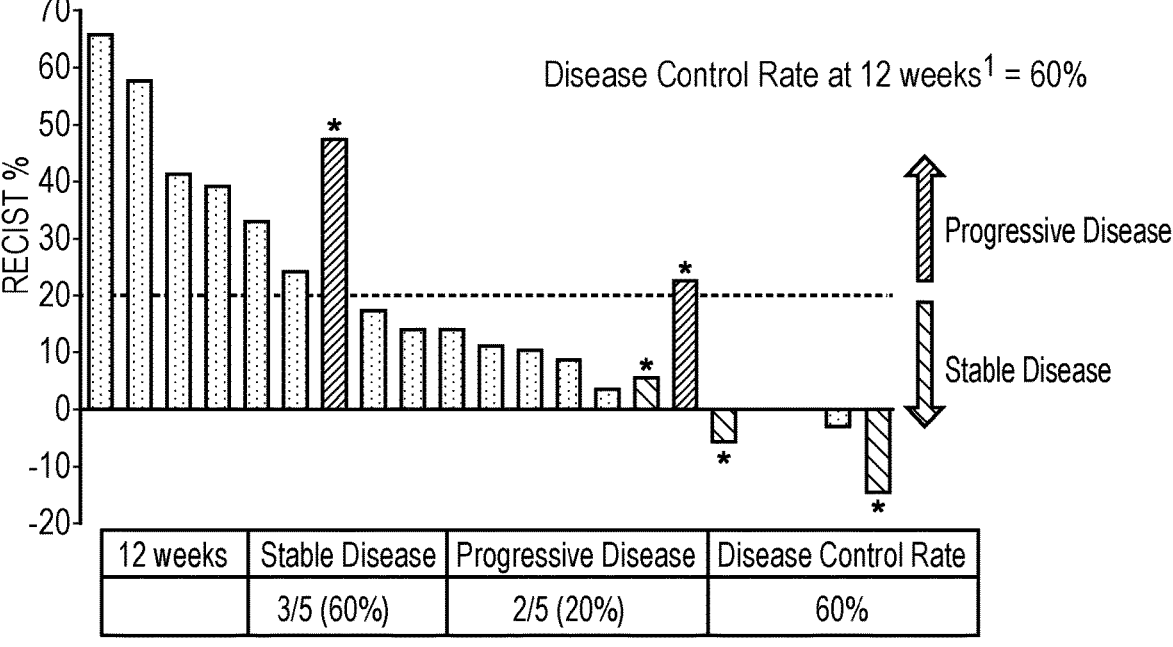
FIG. 10 shows a waterfall plot of the change in RECIST (Response Evaluation Criteria in Solid Tumours) scores in individual ovarian cancer subjects after 6 or 12 weeks of treatment with a MOv18 IgE antibody. The same subjects as shown in FIG. 9 are represented in the same order. Only some (5) subjects continued with treatment beyond 6 weeks. Each vertical bar marked with an asterisk (*) represents the change in RECIST score in an individual subject treated to 12 weeks. The remaining vertical bars without asterisks represent the change in RECIST scores in individual subjects treated to 6 weeks, as shown in FIG. 9. Where no vertical bar is shown, this indicates a change in RECIST score of 0% in the subject (this occurred in two subjects, indicated by the gap in vertical bars along the x-axis).

FIGS. 8 to 10 show that a majority of patients treated with low doses of the MOv18 IgE antibody experienced stable disease. FIG. 8 is a plot of the change in RECIST (Response Evaluation Criteria in Solid Tumours) scores in individual ovarian cancer subjects treated with the MOv18 IgE antibody from the start to end of treatment (0-12 weeks). FIGS. 9 and 10 show the change in RECIST scores in individual subjects at 6 and 12 weeks treatment respectively. A change in RECIST score of less than 20% is indicative of stable disease. After 6 weeks treatment, 70% (14/20) of patients treated had stable disease. 60% (3/5) of patients treated to 12 weeks still had stable disease. Not that the dose frequency dropped from once weekly to once every two weeks in period between 6-12 weeks.

Stable disease (i.e. a change in RECIST score of less than 20%) is a key driver of Progression Free Survival (PFS), an efficacy primary endpoint. The present study indicates a Disease Control Rate of 70% at 6 weeks and 60% at 12 weeks. Thus these results demonstrate that an IgE antibody can be used in humans at a very low dose to treat and/or delay progression of cancer in a subject.

The results show that MOv18 IgE is well suited for anti-cancer therapy and that administration is tolerable in most patients. Most strikingly, the antibody shows anti-tumor activity even at a very low doses (e.g. 700 µg). These results support for the first time the safety and efficacy of IgE as a treatment for cancer, including at unit doses of less than 50 mg (less than 1 mg/kg/week).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A pharmaceutical unit dosage composition comprising 500 µg to 50 mg of a monoclonal antibody of isotype immunoglobulin E (IgE), wherein the monoclonal antibody is a MOv18 IgE monoclonal antibody comprising the light chain variable domain amino acid sequence as defined in SEQ ID NO:3 and the heavy chain variable domain amino acid sequence as defined in SEQ ID NO: 4.

2. The composition according to claim 1, comprising less than 30 mg, less than 25 mg, less than 10 mg, less than 5 mg, less than 3 mg, or less than 1 mg of the monoclonal antibody.

3. The composition according to claim 1, comprising 500 µg to 30 mg, 500 µg to 3 mg, 500 µg to 1 mg, or 700 µg of the monoclonal antibody.

4. The composition according to claim 1, wherein the composition is in the form of a liquid.

5. The composition according to claim 1, comprising an aqueous solution having a concentration of 0.1 mg/ml to 10 mg/ml, 0.5 mg/ml to 2 mg/ml, or 1 mg/ml of the monoclonal antibody.

6. The composition according to claim 1, further comprising one or more pharmaceutically acceptable excipients.

7. The composition according to claim 6, wherein the one or more pharmaceutically acceptable excipients is/are selected from sodium citrate, L-arginine, sucrose, polysorbate 20, and/or sodium chloride.

8. The composition according to claim 1, wherein the composition is suitable for intravenous injection.

9. The composition according to claim 1, wherein the composition is suitable for intravenous injection up to a maximum total dose of 50 mg/week, 25 mg/week, 10 mg/week, 3 mg/week, or 1 mg/week.

10. The composition according to claim 1, wherein the composition comprises less than 3 mg of the monoclonal antibody.

11. A method for treating and/or delaying progression of a folate receptor-positive cancer in a human subject in need thereof, said method comprising administering a pharmaceutical unit dosage composition comprising 500 µg to 50 mg of a monoclonal antibody of isotype immunoglobulin E (IgE), wherein the monoclonal antibody is a MOv18 IgE monoclonal antibody comprising the light chain variable domain amino acid sequence as defined in SEQ ID NO:3 and the heavy chain variable domain amino acid sequence as defined in SEQ ID NO:4.

12. The method according to claim 11, comprising administering a dose of 0.007-0.03 mg/kg/week of the monoclonal antibody to the subject.

13. The method according to claim 11, wherein the method delays progression of an ovarian cancer in the human subject.

14. The method according to claim 11, wherein the cancer is an ovarian cancer.

15. The method according to claim 11, comprising administering a maximum weekly dose of 50 mg, 25 mg, 10 mg, 3 mg, or 1 mg of the monoclonal antibody to the subject.

16. The method according to claim 15, wherein the weekly dose of the monoclonal antibody is 500 µg to 50 mg, 500 µg to 30 mg, 500 µg to 3 mg, 500 µg to 1 mg, or 700 µg.

17. The method according to claim 11, comprising administering the monoclonal antibody to the subject once a week or once every two weeks.

18. The method according to claim 17, comprising administering the monoclonal antibody to the subject for less than or equal to 12 weeks.

19. The method according to claim 18, comprising administering the monoclonal antibody to the subject (i) once a week for 6 weeks; followed by (ii) once every two weeks for 6 weeks.

20. The method according to claim 11, comprising administering the monoclonal antibody to the subject in a dose per administration of less than 1 mg/kg, less than 0.1 mg/kg, or less than 0.03 mg/kg.

21. The method according to claim 11, comprising administering the monoclonal antibody to the subject in a dose of less than 1 mg/kg/week, less than 0.1 mg/kg/week, or less than 0.03 mg/kg/week.

* * * * *

SEQUENCE LISTING

```
<160> NUMBER OF SEQ ID NOS: 141

<210> SEQ ID NO 1
<211> LENGTH: 209
<212> TYPE: PRT
<213> ORGANISM: Artificial Sequence
<220> FEATURE:
<223> OTHER INFORMATION: MOv18 IgE Light (L) Chain

<400> SEQUENCE: 1

Gln Thr Thr Ser Ser Leu Ser Ala Ser Leu Gly Asp Arg Val Thr Ile
1               5                   10                  15

Ser Cys Arg Ala Ser Gln Asp Ile Asn Asn Phe Leu Asn Trp Tyr Gln
            20                  25                  30

Gln Lys Pro Asp Gly Thr Val Lys Leu Leu Ile Tyr Tyr Thr Ser Arg
        35                  40                  45

Leu His Ser Gly Val Pro Ser Arg Phe Ser Gly Ser Gly Ser Gly Thr
    50                  55                  60

Asp Tyr Ser Leu Thr Ile Ile Asn Leu Glu Gln Glu Asp Ile Ala Ile
65                  70                  75                  80

Tyr Phe Cys Gln Gln Ser Ser Thr Ile Pro Arg Thr Phe Gly Gly Gly
            85                  90                  95

Thr Lys Leu Glu Ile Lys Arg Thr Val Ala Ala Pro Ser Val Phe Ile
        100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln Trp Lys
    130                 135                 140

Val Asp Asn Ala Leu Gln Ser Gly Asn Ser Gln Glu Ser Val Thr Glu
145                 150                 155                 160

Gln Asp Ser Lys Asp Ser Thr Tyr Ser Leu Ser Ser Thr Leu Thr Leu
            165                 170                 175

Ser Lys Ala Asp Tyr Glu Lys His Lys Val Tyr Ala Cys Glu Val Thr
            180                 185                 190

His Gln Gly Leu Ser Ser Pro Val Thr Lys Ser Phe Asn Arg Gly Glu
        195                 200                 205

Cys

<210> SEQ ID NO 2
<211> LENGTH: 549
<212> TYPE: PRT
<213> ORGANISM: Artificial Sequence
<220> FEATURE:
<223> OTHER INFORMATION: MOv18 IgE Heavy (H) Chain

<400> SEQUENCE: 2

Gln Val Gln Leu Gln Gln Ser Gly Ala Glu Leu Ala Arg Pro Gly Ala
```

```
1                  5                    10                    15

Ser Val Lys Leu Ser Cys Lys Ala Ser Asp Tyr Ile Phe Thr Asn Tyr
            20                  25                  30

Asp Ile Thr Trp Val Lys Gln Arg Pro Gly Gln Gly Leu Glu Trp Ile
            35                  40                  45

Gly Glu Ile Asp Pro Arg Ser Gly Lys Ser Tyr Tyr Asn Glu Lys Phe
    50                  55                  60

Lys Gly Lys Ser Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Thr Met Tyr Tyr Tyr Gly Ser Ser Pro Pro Met Asp Tyr Trp Gly
            100                 105                 110

Gln Gly Thr Ser Val Thr Val Ser Ser Ala Ser Thr Gln Ser Pro Ser
            115                 120                 125

Val Phe Pro Leu Thr Arg Cys Cys Lys Asn Ile Pro Ser Asn Ala Thr
    130                 135                 140

Ser Val Thr Leu Gly Cys Leu Ala Thr Gly Tyr Phe Pro Glu Pro Val
145                 150                 155                 160

Met Val Thr Trp Asp Thr Gly Ser Leu Asn Gly Thr Thr Met Thr Leu
                165                 170                 175

Pro Ala Thr Thr Leu Thr Leu Ser Gly His Tyr Ala Thr Ile Ser Leu
            180                 185                 190

Leu Thr Val Ser Gly Ala Trp Ala Lys Gln Met Phe Thr Cys Arg Val
            195                 200                 205

Ala His Thr Pro Ser Ser Thr Asp Trp Val Asp Asn Lys Thr Phe Ser
    210                 215                 220

Val Cys Ser Arg Asp Phe Thr Pro Pro Thr Val Lys Ile Leu Gln Ser
225                 230                 235                 240

Ser Cys Asp Gly Gly Gly His Phe Pro Pro Thr Ile Gln Leu Leu Cys
            245                 250                 255

Leu Val Ser Gly Tyr Thr Pro Gly Thr Ile Asn Ile Thr Trp Leu Glu
            260                 265                 270

Asp Gly Gln Val Met Asp Val Asp Leu Ser Thr Ala Ser Thr Thr Gln
    275                 280                 285

Glu Gly Glu Leu Ala Ser Thr Gln Ser Glu Leu Thr Leu Ser Gln Lys
    290                 295                 300

His Trp Leu Ser Asp Arg Thr Tyr Thr Cys Gln Val Thr Tyr Gln Gly
305                 310                 315                 320

His Thr Phe Glu Asp Ser Thr Lys Lys Cys Ala Asp Ser Asn Pro Arg
            325                 330                 335

Gly Val Ser Ala Tyr Leu Ser Arg Pro Ser Pro Phe Asp Leu Phe Ile
            340                 345                 350

Arg Lys Ser Pro Thr Ile Thr Cys Leu Val Val Asp Leu Ala Pro Ser
            355                 360                 365

Lys Gly Thr Val Asn Leu Thr Trp Ser Arg Ala Ser Gly Lys Pro Val
    370                 375                 380

Asn His Ser Thr Arg Lys Glu Glu Lys Gln Arg Asn Gly Thr Leu Thr
385                 390                 395                 400

Val Thr Ser Thr Leu Pro Val Gly Thr Arg Asp Trp Ile Glu Gly Glu
                405                 410                 415

Thr Tyr Gln Cys Arg Val Thr His Pro His Leu Pro Arg Ala Leu Met
            420                 425                 430
```

-continued

```
Arg Ser Thr Thr Lys Thr Ser Gly Pro Arg Ala Ala Pro Glu Val Tyr
        435             440             445

Ala Phe Ala Thr Pro Glu Trp Pro Gly Ser Arg Asp Lys Arg Thr Leu
        450             455             460

Ala Cys Leu Ile Gln Asn Phe Met Pro Glu Asp Ile Ser Val Gln Trp
465             470             475             480

Leu His Asn Glu Val Gln Leu Pro Asp Ala Arg His Ser Thr Thr Gln
                485             490             495

Pro Arg Lys Thr Lys Gly Ser Gly Phe Phe Val Phe Ser Arg Leu Glu
            500             505             510

Val Thr Arg Ala Glu Trp Glu Gln Lys Asp Glu Phe Ile Cys Arg Ala
        515             520             525

Val His Glu Ala Ala Ser Pro Ser Gln Thr Val Gln Arg Ala Val Ser
    530             535             540

Val Asn Pro Gly Lys
545

<210> SEQ ID NO 3
<211> LENGTH: 107
<212> TYPE: PRT
<213> ORGANISM: Artificial Sequence
<220> FEATURE:
<223> OTHER INFORMATION: MOv18 IgE Light Chain Variable Domain

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Phe
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ile Asn Leu Glu Gln
65                  70                  75                  80

Glu Asp Ile Ala Ile Tyr Phe Cys Gln Gln Ser Ser Thr Ile Pro Arg
                85                  90                  95

Thr Phe Gly Gly Gly Thr Lys Leu Glu Ile Lys
            100             105

<210> SEQ ID NO 4
<211> LENGTH: 121
<212> TYPE: PRT
<213> ORGANISM: Artificial Sequence
<220> FEATURE:
<223> OTHER INFORMATION: MOv18 IgE Heavy Chain Variable Domain

<400> SEQUENCE: 4

Gln Val Gln Leu Gln Gln Ser Gly Ala Glu Leu Ala Arg Pro Gly Ala
1               5                   10                  15

Ser Val Lys Leu Ser Cys Lys Ala Ser Asp Tyr Ile Phe Thr Asn Tyr
            20                  25                  30

Asp Ile Thr Trp Val Lys Gln Arg Pro Gly Gln Gly Leu Glu Trp Ile
        35                  40                  45

Gly Glu Ile Asp Pro Arg Ser Gly Lys Ser Tyr Tyr Asn Glu Lys Phe
    50                  55                  60

Lys Gly Lys Ser Thr Leu Thr Ala Asp Lys Ser Ser Ser Thr Ala Tyr
```

-continued

```
65                 70                 75                 80

Met Glu Leu Arg Ser Leu Thr Ser Glu Asp Ser Ala Val Tyr Phe Cys
                85                  90                  95

Ala Thr Met Tyr Tyr Tyr Gly Ser Ser Pro Pro Met Asp Tyr Trp Gly
            100                 105                 110

Gln Gly Thr Ser Val Thr Val Ser Ser
        115                 120

<210> SEQ ID NO 5
<211> LENGTH: 12
<212> TYPE: PRT
<213> ORGANISM: Artificial Sequence
<220> FEATURE:
<223> OTHER INFORMATION: Palivizumab CDR H1

<400> SEQUENCE: 5

Gly Phe Ser Leu Ser Thr Ser Gly Met Ser Val Gly
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Palivizumab CDR H2

<400> SEQUENCE: 6

Asp Ile Trp Trp Asp Asp Lys Lys Asp Tyr Asn Pro Ser Leu Lys Ser
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Palivizumab CDR H3

<400> SEQUENCE: 7

Ser Met Ile Thr Asn Trp Tyr Phe Asp Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Palivizumab CDR L1

<400> SEQUENCE: 8

Lys Cys Gln Leu Ser Val Gly Tyr Met His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Palivizumab CDR L2

<400> SEQUENCE: 9

Asp Thr Ser Lys Leu Ala Ser
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: Palivizumab CDR L3

<400> SEQUENCE: 10

Phe Gln Gly Ser Gly Tyr Pro Phe Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Ranibizumab CDR H1

<400> SEQUENCE: 11

Gly Tyr Asp Phe Thr His Tyr Gly Met Asn
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Ranibizumab CDR H2

<400> SEQUENCE: 12

Trp Ile Asn Thr Tyr Thr Gly Glu Pro Thr Tyr Ala Ala Asp Phe Lys
1               5                   10                  15

Arg

<210> SEQ ID NO 13
<211> LENGTH: 13
<212> TYPE: PRT
<213> ORGANISM: Artificial Sequence
<220> FEATURE:
<223> OTHER INFORMATION: Ranibizumab CDR H3

<400> SEQUENCE: 13

Tyr Pro Tyr Tyr Tyr Gly Thr Ser His Trp Phe Asp Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: L1

<400> SEQUENCE: 14

Ser Ala Ser Gln Asp Ile Ser Asn Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Ranibizumab CDR L2

<400> SEQUENCE: 15

Phe Thr Ser Ser Leu His Ser
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Ranibizumab CDR L3

<400> SEQUENCE: 16

Gln Gln Tyr Ser Thr Val Pro Trp Thr
1               5

<210> SEQ ID NO 17
<211> LENGTH: 8
<212> TYPE: PRT
<213> ORGANISM: Artificial Sequence
<220> FEATURE:
<223> OTHER INFORMATION: HMW-MAA CDR H1

<400> SEQUENCE: 17

Gly Phe Thr Phe Ser Asn Tyr Trp
1               5

<210> SEQ ID NO 18
<211> LENGTH: 10
<212> TYPE: PRT
<213> ORGANISM: Artificial Sequence
<220> FEATURE:
<223> OTHER INFORMATION: HMW-MAA CDR H2

<400> SEQUENCE: 18

Ile Arg Leu Lys Ser Asn Asn Phe Gly Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: HMW-MAA CDR H3

<400> SEQUENCE: 19

Thr Ser Tyr Gly Asn Tyr Val Gly His Tyr Phe Asp His
1               5                   10

<210> SEQ ID NO 20
<211> LENGTH: 6
<212> TYPE: PRT
<213> ORGANISM: Artificial Sequence
<220> FEATURE:
<223> OTHER INFORMATION: HMW-MAA CDR L1

<400> SEQUENCE: 20

Gln Asn Val Asp Thr Asn
1               5

<210> SEQ ID NO 21
<211> LENGTH: 3
<212> TYPE: PRT
<213> ORGANISM: Artificial Sequence
<220> FEATURE:
<223> OTHER INFORMATION: HMW-MAA CDR L2

<400> SEQUENCE: 21

Ser Ala Ser
1

<210> SEQ ID NO 22
<211> LENGTH: 9
```

```
<212> TYPE: PRT
<213> ORGANISM: Artificial Sequence
<220> FEATURE:
<223> OTHER INFORMATION: HMW-MAA CDR L3

<400> SEQUENCE: 22

Gln Gln Tyr Asn Ser Tyr Pro Leu Thr
1               5

<210> SEQ ID NO 23
<211> LENGTH: 123
<212> TYPE: PRT
<213> ORGANISM: Artificial Sequence
<220> FEATURE:
<223> OTHER INFORMATION: HMW-MAA Variable Domain (Heavy Chain)

<400> SEQUENCE: 23

Glu Gln Val Lys Leu Gln Gln Ser Gly Gly Gly Leu Val Gln Pro Gly
1               5                   10                  15

Gly Ser Met Lys Leu Ser Cys Val Val Ser Gly Phe Thr Phe Ser Asn
                20                  25                  30

Tyr Trp Met Asn Trp Val Arg Gln Ser Pro Glu Lys Gly Leu Glu Trp
            35                  40                  45

Ile Ala Glu Ile Arg Leu Lys Ser Asn Asn Phe Gly Arg Tyr Tyr Ala
    50                  55                  60

Glu Ser Val Lys Gly Arg Phe Thr Ile Ser Arg Asp Asp Ser Lys Ser
65                  70                  75                  80

Ser Ala Tyr Leu Gln Met Ile Asn Leu Arg Ala Glu Asp Thr Gly Ile
                85                  90                  95

Tyr Tyr Cys Thr Ser Tyr Gly Asn Tyr Val Gly His Tyr Phe Asp His
                100                 105                 110

Trp Gly Gln Gly Thr Thr Val Thr Val Ser Ser
            115                 120

<210> SEQ ID NO 24
<211> LENGTH: 122
<212> TYPE: PRT
<213> ORGANISM: Artificial Sequence
<220> FEATURE:
<223> OTHER INFORMATION: HMW-MAA Alternative Variable Domain (Heavy
      Chain)

<400> SEQUENCE: 24

Glu Val Gln Leu Val Gln Ser Gly Gly Gly Leu Val Gln Pro Gly Gly
1               5                   10                  15

Ser Leu Lys Leu Ser Cys Ala Val Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Gly Glu Ile Arg Leu Lys Ser Asn Asn Phe Gly Arg Tyr Tyr Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Tyr Gly Asn Tyr Val Gly His Tyr Phe Asp His Trp
                100                 105                 110

Gly Gln Gly Thr Leu Val Thr Val Ser Ser
            115                 120
```

```
<210> SEQ ID NO 25
<211> LENGTH: 107
<212> TYPE: PRT
<213> ORGANISM: Artificial Sequence
<220> FEATURE:
<223> OTHER INFORMATION: HMW-MAA Variable Domain (Light Chain)

<400> SEQUENCE: 25

Asp Ile Glu Leu Thr Gln Ser Pro Lys Phe Met Ser Thr Ser Val Cys
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: HMW-MAA Alternative Variable Domain (Light
      Chain)

<400> SEQUENCE: 26

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Pro Leu Leu
        35                  40                  45

Phe Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 27
<211> LENGTH: 8
<212> TYPE: PRT
<213> ORGANISM: Artificial Sequence
<220> FEATURE:
<223> OTHER INFORMATION: Alemtuzumab CDR H1

<400> SEQUENCE: 27

Gly Phe Thr Phe Thr Asp Phe Tyr
1               5

<210> SEQ ID NO 28
<211> LENGTH: 10
```

```
<212> TYPE: PRT
<213> ORGANISM: Artificial Sequence
<220> FEATURE:
<223> OTHER INFORMATION: Alemtuzumab CDR H2

<400> SEQUENCE: 28

Ile Arg Asp Lys Ala Lys Gly Tyr Thr Thr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Alemtuzumab CDR H3

<400> SEQUENCE: 29

Ala Arg Glu Gly His Thr Ala Ala Pro Phe Asp Tyr
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Alemtuzumab CDR L1

<400> SEQUENCE: 30

Gln Asn Ile Asp Lys Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Alemtuzumab CDR L2

<400> SEQUENCE: 31

Asn Thr Asn
1

<210> SEQ ID NO 32
<211> LENGTH: 9
<212> TYPE: PRT
<213> ORGANISM: Artificial Sequence
<220> FEATURE:
<223> OTHER INFORMATION: Alemtuzumab CDR L3

<400> SEQUENCE: 32

Leu Gln His Ile Ser Arg Pro Arg Thr
1               5

<210> SEQ ID NO 33
<211> LENGTH: 5
<212> TYPE: PRT
<213> ORGANISM: Artificial Sequence
<220> FEATURE:
<223> OTHER INFORMATION: Atezolizumab CDR H1

<400> SEQUENCE: 33

Asp Ser Trp Ile His
1               5

<210> SEQ ID NO 34
<211> LENGTH: 10
<212> TYPE: PRT
```

<213> ORGANISM: Artificial Sequence
<220> FEATURE:
<223> OTHER INFORMATION: Atezolizumab CDR H2

<400> SEQUENCE: 34

Trp Ile Ser Pro Tyr Gly Gly Ser Thr Tyr
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Atezolizumab CDR H3

<400> SEQUENCE: 35

Arg His Trp Pro Gly Gly Phe
1               5

<210> SEQ ID NO 36
<211> LENGTH: 7
<212> TYPE: PRT
<213> ORGANISM: Artificial Sequence
<220> FEATURE:
<223> OTHER INFORMATION: Atezolizumab CDR L1

<400> SEQUENCE: 36

Asp Val Ser Thr Ala Val Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Atezolizumab CDR L2

<400> SEQUENCE: 37

Ser Ala Ser Phe Leu Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Atezolizumab CDR L3

<400> SEQUENCE: 38

Gln Gln Tyr Leu Tyr His Pro Ala Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Avelumab CDR H1

<400> SEQUENCE: 39

Ser Tyr Ile Met Met
1               5

<210> SEQ ID NO 40
<211> LENGTH: 10
<212> TYPE: PRT
<213> ORGANISM: Artificial Sequence

```
<220> FEATURE:
<223> OTHER INFORMATION: Avelumab CDR H2

<400> SEQUENCE: 40

Ser Ile Tyr Pro Ser Gly Gly Ile Thr Phe
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Avelumab CDR H3

<400> SEQUENCE: 41

Ile Lys Leu Phe Thr Val Thr Thr Val
1               5

<210> SEQ ID NO 42
<211> LENGTH: 8
<212> TYPE: PRT
<213> ORGANISM: Artificial Sequence
<220> FEATURE:
<223> OTHER INFORMATION: Avelumab CDR L1

<400> SEQUENCE: 42

Val Gly Gly Tyr Asn Tyr Val Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Avelumab CDR L2

<400> SEQUENCE: 43

Asp Val Ser Asn Arg Pro
1               5

<210> SEQ ID NO 44
<211> LENGTH: 6
<212> TYPE: PRT
<213> ORGANISM: Artificial Sequence
<220> FEATURE:
<223> OTHER INFORMATION: Avelumab CDR L2

<400> SEQUENCE: 44

Asp Val Ser Asn Arg Pro
1               5

<210> SEQ ID NO 45
<211> LENGTH: 10
<212> TYPE: PRT
<213> ORGANISM: Artificial Sequence
<220> FEATURE:
<223> OTHER INFORMATION: Avelumab CDR L3

<400> SEQUENCE: 45

Ser Ser Tyr Thr Ser Ser Ser Thr Arg Val
1               5                   10

<210> SEQ ID NO 46
<211> LENGTH: 8
<212> TYPE: PRT
<213> ORGANISM: Artificial Sequence
<220> FEATURE:
```

-continued

```
<223> OTHER INFORMATION: Bevacizumab CDR H1

<400> SEQUENCE: 46

Gly Tyr Thr Phe Thr Asn Tyr Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Bevacizumab CDR H2

<400> SEQUENCE: 47

Ile Asn Thr Tyr Thr Gly Glu Pro
1               5

<210> SEQ ID NO 48
<211> LENGTH: 16
<212> TYPE: PRT
<213> ORGANISM: Artificial Sequence
<220> FEATURE:
<223> OTHER INFORMATION: Bevacizumab CDR H3

<400> SEQUENCE: 48

Ala Lys Tyr Pro His Tyr Tyr Gly Ser Ser His Trp Tyr Phe Asp Val
1               5                   10                  15

<210> SEQ ID NO 49
<211> LENGTH: 6
<212> TYPE: PRT
<213> ORGANISM: Artificial Sequence
<220> FEATURE:
<223> OTHER INFORMATION: Bevacizumab CDR L1

<400> SEQUENCE: 49

Gln Asp Ile Ser Asn Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: Bevacizumab CDR L2

<400> SEQUENCE: 50

Phe Thr Ser
1

<210> SEQ ID NO 51
<211> LENGTH: 9
<212> TYPE: PRT
<213> ORGANISM: Artificial Sequence
<220> FEATURE:
<223> OTHER INFORMATION: Bevacizumab CDR L3

<400> SEQUENCE: 51

Gln Gln Tyr Ser Thr Val Pro Trp Thr
1               5

<210> SEQ ID NO 52
<211> LENGTH: 10
<212> TYPE: PRT
<213> ORGANISM: Artificial Sequence
<220> FEATURE:
<223> OTHER INFORMATION: Certolizumab CDR H1
```

<400> SEQUENCE: 52

Gly Tyr Val Phe Thr Asp Tyr Gly Met Asn
1               5                   10

<210> SEQ ID NO 53
<211> LENGTH: 18
<212> TYPE: PRT
<213> ORGANISM: Artificial Sequence
<220> FEATURE:
<223> OTHER INFORMATION: Certolizumab CDR H2

<400> SEQUENCE: 53

Gly Trp Ile Asn Thr Tyr Ile Gly Glu Pro Ile Tyr Ala Asp Ser Val
1               5                   10                  15

Lys Gly

<210> SEQ ID NO 54
<211> LENGTH: 11
<212> TYPE: PRT
<213> ORGANISM: Artificial Sequence
<220> FEATURE:
<223> OTHER INFORMATION: Certolizumab CDR H3

<400> SEQUENCE: 54

Ala Arg Gly Tyr Arg Ser Tyr Ala Met Asp Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Certolizumab CDR L1

<400> SEQUENCE: 55

Lys Ala Ser Gln Asn Val Gly Thr Asn Val Ala
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Certolizumab CDR L2

<400> SEQUENCE: 56

Ser Ala Ser Phe Leu Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: Certolizumab CDR L3

<400> SEQUENCE: 57

Gln Gln Tyr Asn Ile Tyr Pro Leu
1               5

<210> SEQ ID NO 58
<211> LENGTH: 8
<212> TYPE: PRT
<213> ORGANISM: Artificial Sequence
<220> FEATURE:

<223> OTHER INFORMATION: Cetuximab CDR H1

<400> SEQUENCE: 58

Gly Phe Ser Leu Thr Asn Tyr Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Cetuximab CDR H2

<400> SEQUENCE: 59

Ile Trp Ser Gly Gly Asn Thr
1               5

<210> SEQ ID NO 60
<211> LENGTH: 13
<212> TYPE: PRT
<213> ORGANISM: Artificial Sequence
<220> FEATURE:
<223> OTHER INFORMATION: Cetuximab CDR H3

<400> SEQUENCE: 60

Ala Arg Ala Leu Thr Tyr Tyr Asp Tyr Glu Phe Ala Tyr
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Cetuximab CDR L1

<400> SEQUENCE: 61

Gln Ser Ile Gly Thr Asn
1               5

<210> SEQ ID NO 62
<211> LENGTH: 3
<212> TYPE: PRT
<213> ORGANISM: Artificial Sequence
<220> FEATURE:
<223> OTHER INFORMATION: Cetuximab CDR L2

<400> SEQUENCE: 62

Tyr Ala Ser
1

<210> SEQ ID NO 63
<211> LENGTH: 9
<212> TYPE: PRT
<213> ORGANISM: Artificial Sequence
<220> FEATURE:
<223> OTHER INFORMATION: Cetuximab CDR L3

<400> SEQUENCE: 63

Gln Gln Asn Asn Asn Trp Pro Thr Thr
1               5

<210> SEQ ID NO 64
<211> LENGTH: 5
<212> TYPE: PRT
<213> ORGANISM: Artificial Sequence
<220> FEATURE:
<223> OTHER INFORMATION: Durvalumab CDR H1

<400> SEQUENCE: 64

Arg Tyr Trp Met Ser
1               5

<210> SEQ ID NO 65
<211> LENGTH: 10
<212> TYPE: PRT
<213> ORGANISM: Artificial Sequence
<220> FEATURE:
<223> OTHER INFORMATION: Durvalumab CDR H2

<400> SEQUENCE: 65

Asn Ile Lys Gln Asp Gly Ser Glu Lys Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Durvalumab CDR H3

<400> SEQUENCE: 66

Glu Gly Gly Trp Phe Gly Glu Leu Ala Phe
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Durvalumab CDR L1

<400> SEQUENCE: 67

Arg Val Ser Ser Ser Tyr Leu Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Durvalumab CDR L2

<400> SEQUENCE: 68

Asp Ala Ser Ser Arg Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Durvalumab CDR L3

<400> SEQUENCE: 69

Gln Gln Tyr Gly Ser Leu Pro Trp Thr
1               5

<210> SEQ ID NO 70
<211> LENGTH: 10
<212> TYPE: PRT
<213> ORGANISM: Artificial Sequence
<220> FEATURE:
<223> OTHER INFORMATION: Efalizumab CDR H1

58

-continued

```
<400> SEQUENCE: 70

Gly Tyr Ser Phe Thr Gly His Trp Met Asn
1               5                   10

<210> SEQ ID NO 71
<211> LENGTH: 20
<212> TYPE: PRT
<213> ORGANISM: Artificial Sequence
<220> FEATURE:
<223> OTHER INFORMATION: Efalizumab CDR H2

<400> SEQUENCE: 71

Gly Ile Met Ile His Pro Ser Asp Ser Glu Thr Arg Tyr Asn Gln Lys
1               5                   10                  15

Phe Lys Asp Ile
            20

<210> SEQ ID NO 72
<211> LENGTH: 16
<212> TYPE: PRT
<213> ORGANISM: Artificial Sequence
<220> FEATURE:
<223> OTHER INFORMATION: Efalizumab CDR H3

<400> SEQUENCE: 72

Ala Arg Ile Gly Ile Tyr Phe Tyr Gly Thr Thr Tyr Phe Asp Tyr Ile
1               5                   10                  15

<210> SEQ ID NO 73
<211> LENGTH: 11
<212> TYPE: PRT
<213> ORGANISM: Artificial Sequence
<220> FEATURE:
<223> OTHER INFORMATION: Efalizumab CDR L1

<400> SEQUENCE: 73

Arg Ala Ser Lys Thr Ile Ser Lys Tyr Leu Ala
1               5                   10

<210> SEQ ID NO 74
<211> LENGTH: 6
<212> TYPE: PRT
<213> ORGANISM: Artificial Sequence
<220> FEATURE:
<223> OTHER INFORMATION: Efalizumab CDR L2

<400> SEQUENCE: 74

Ser Gly Ser Thr Leu Gln
1               5

<210> SEQ ID NO 75
<211> LENGTH: 8
<212> TYPE: PRT
<213> ORGANISM: Artificial Sequence
<220> FEATURE:
<223> OTHER INFORMATION: Efalizumab CDR L3

<400> SEQUENCE: 75

Gln Gln His Asn Glu Tyr Pro Leu
1               5

<210> SEQ ID NO 76
<211> LENGTH: 11
<212> TYPE: PRT
<213> ORGANISM: Artificial Sequence
<220> FEATURE:
```

-continued

<223> OTHER INFORMATION: Omalizumab CDR H1

<400> SEQUENCE: 76

Gly Tyr Ser Ile Thr Ser Gly Tyr Ser Trp Asn
1               5                   10

<210> SEQ ID NO 77
<211> LENGTH: 17
<212> TYPE: PRT
<213> ORGANISM: Artificial Sequence
<220> FEATURE:
<223> OTHER INFORMATION: Omalizumab CDR H2

<400> SEQUENCE: 77

Ala Ser Ile Thr Tyr Asp Gly Ser Thr Asn Tyr Ala Asp Ser Val Lys
1               5                   10                  15

Gly

<210> SEQ ID NO 78
<211> LENGTH: 14
<212> TYPE: PRT
<213> ORGANISM: Artificial Sequence
<220> FEATURE:
<223> OTHER INFORMATION: Omalizumab CDR H3

<400> SEQUENCE: 78

Ala Arg Gly Ser His Tyr Phe Gly His Trp His Phe Ala Val
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Omalizumab CDR L1

<400> SEQUENCE: 79

Arg Ala Ser Gln Ser Val Asp Tyr Asp Gly Asp Ser Tyr Met Asn
1               5                   10                  15

<210> SEQ ID NO 80
<211> LENGTH: 6
<212> TYPE: PRT
<213> ORGANISM: Artificial Sequence
<220> FEATURE:
<223> OTHER INFORMATION: Omalizumab CDR L2

<400> SEQUENCE: 80

Ala Ala Ser Tyr Leu Glu
1               5

<210> SEQ ID NO 81
<211> LENGTH: 8
<212> TYPE: PRT
<213> ORGANISM: Artificial Sequence
<220> FEATURE:
<223> OTHER INFORMATION: Omalizumab CDR L3

<400> SEQUENCE: 81

Gln Gln Ser His Glu Asp Pro Tyr
1               5

<210> SEQ ID NO 82
<211> LENGTH: 10
<212> TYPE: PRT
<213> ORGANISM: Artificial Sequence -continued

```
<220> FEATURE:
<223> OTHER INFORMATION: Panitumumab CDR H1

<400> SEQUENCE: 82

Gly Gly Ser Val Ser Ser Gly Asp Tyr Tyr
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Panitumumab CDR H2

<400> SEQUENCE: 83

Ile Tyr Tyr Ser Gly Asn Thr
1               5

<210> SEQ ID NO 84
<211> LENGTH: 11
<212> TYPE: PRT
<213> ORGANISM: Artificial Sequence
<220> FEATURE:
<223> OTHER INFORMATION: Panitumumab CDR H3

<400> SEQUENCE: 84

Val Arg Asp Arg Val Thr Gly Ala Phe Asp Ile
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Panitumumab CDR L1

<400> SEQUENCE: 85

Gln Asp Ile Ser Asn Tyr
1               5

<210> SEQ ID NO 86
<211> LENGTH: 3
<212> TYPE: PRT
<213> ORGANISM: Artificial Sequence
<220> FEATURE:
<223> OTHER INFORMATION: Panitumumab CDR L2

<400> SEQUENCE: 86

Asp Ala Ser
1

<210> SEQ ID NO 87
<211> LENGTH: 9
<212> TYPE: PRT
<213> ORGANISM: Artificial Sequence
<220> FEATURE:
<223> OTHER INFORMATION: Panitumumab CDR L3

<400> SEQUENCE: 87

Gln His Phe Asp His Leu Pro Leu Ala
1               5

<210> SEQ ID NO 88
<211> LENGTH: 8
<212> TYPE: PRT
<213> ORGANISM: Artificial Sequence
<220> FEATURE:
```

<223> OTHER INFORMATION: Pertuzumab CDR L1

<400> SEQUENCE: 88

Gly Phe Thr Phe Thr Asp Tyr Thr
1               5

<210> SEQ ID NO 89
<211> LENGTH: 8
<212> TYPE: PRT
<213> ORGANISM: Artificial Sequence
<220> FEATURE:
<223> OTHER INFORMATION: Pertuzumab CDR H2

<400> SEQUENCE: 89

Val Asn Pro Asn Ser Gly Gly Ser
1               5

<210> SEQ ID NO 90
<211> LENGTH: 12
<212> TYPE: PRT
<213> ORGANISM: Artificial Sequence
<220> FEATURE:
<223> OTHER INFORMATION: Pertuzumab CDR H3

<400> SEQUENCE: 90

Ala Arg Asn Leu Gly Pro Ser Phe Tyr Phe Asp Tyr
1               5                   10

<210> SEQ ID NO 91
<211> LENGTH: 6
<212> TYPE: PRT
<213> ORGANISM: Artificial Sequence
<220> FEATURE:
<223> OTHER INFORMATION: Pertuzumab CDR L1

<400> SEQUENCE: 91

Gln Asp Val Ser Ile Gly
1               5

<210> SEQ ID NO 92
<211> LENGTH: 3
<212> TYPE: PRT
<213> ORGANISM: Artificial Sequence
<220> FEATURE:
<223> OTHER INFORMATION: Pertuzumab CDR L2

<400> SEQUENCE: 92

Ser Ala Ser
1

<210> SEQ ID NO 93
<211> LENGTH: 9
<212> TYPE: PRT
<213> ORGANISM: Artificial Sequence
<220> FEATURE:
<223> OTHER INFORMATION: Pertuzumab CDR L3

<400> SEQUENCE: 93

Gln Gln Tyr Tyr Ile Tyr Pro Tyr Thr
1               5

<210> SEQ ID NO 94
<211> LENGTH: 8
<212> TYPE: PRT
<213> ORGANISM: Artificial Sequence
<220> FEATURE:
<223> OTHER INFORMATION: Rituximab CDR H1

<400> SEQUENCE: 94

Gly Tyr Thr Phe Thr Ser Tyr Asn
1               5

<210> SEQ ID NO 95
<211> LENGTH: 8
<212> TYPE: PRT
<213> ORGANISM: Artificial Sequence
<220> FEATURE:
<223> OTHER INFORMATION: Rituximab CDR H2

<400> SEQUENCE: 95

Ile Tyr Pro Gly Asn Gly Asp Thr
1               5

<210> SEQ ID NO 96
<211> LENGTH: 13
<212> TYPE: PRT
<213> ORGANISM: Artificial Sequence
<220> FEATURE:
<223> OTHER INFORMATION: Rituximab CDR H3

<400> SEQUENCE: 96

Ala Arg Ser Thr Tyr Tyr Gly Gly Asp Trp Phe Asn Val
1               5                   10

<210> SEQ ID NO 97
<211> LENGTH: 5
<212> TYPE: PRT
<213> ORGANISM: Artificial Sequence
<220> FEATURE:
<223> OTHER INFORMATION: Rituximab CDR L1

<400> SEQUENCE: 97

Ser Ser Val Ser Tyr
1               5

<210> SEQ ID NO 98
<211> LENGTH: 3
<212> TYPE: PRT
<213> ORGANISM: Artificial Sequence
<220> FEATURE:
<223> OTHER INFORMATION: Rituximab CDR L2

<400> SEQUENCE: 98

Ala Thr Ser
1

<210> SEQ ID NO 99
<211> LENGTH: 9
<212> TYPE: PRT
<213> ORGANISM: Artificial Sequence
<220> FEATURE:
<223> OTHER INFORMATION: Rituximab CDR L3

<400> SEQUENCE: 99

Gln Gln Trp Thr Ser Asn Pro Pro Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Trastuzumab CDR H1

```
<400> SEQUENCE: 100

Gly Phe Asn Ile Lys Asp Thr Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: Trastuzumab CDR H2

<400> SEQUENCE: 101

Ile Tyr Pro Thr Asn Gly Tyr Thr
1               5

<210> SEQ ID NO 102
<211> LENGTH: 13
<212> TYPE: PRT
<213> ORGANISM: Artificial Sequence
<220> FEATURE:
<223> OTHER INFORMATION: Trastuzumab CDR H3

<400> SEQUENCE: 102

Ser Arg Trp Gly Gly Asp Gly Phe Tyr Ala Met Asp Tyr
1               5                   10

<210> SEQ ID NO 103
<211> LENGTH: 6
<212> TYPE: PRT
<213> ORGANISM: Artificial Sequence
<220> FEATURE:
<223> OTHER INFORMATION: Trastuzumab CDR L1

<400> SEQUENCE: 103

Gln Asp Val Asn Thr Ala
1               5

<210> SEQ ID NO 104
<211> LENGTH: 3
<212> TYPE: PRT
<213> ORGANISM: Artificial Sequence
<220> FEATURE:
<223> OTHER INFORMATION: Trastuzumab CDR L2

<400> SEQUENCE: 104

Ser Ala Ser
1

<210> SEQ ID NO 105
<211> LENGTH: 9
<212> TYPE: PRT
<213> ORGANISM: Artificial Sequence
<220> FEATURE:
<223> OTHER INFORMATION: L3

<400> SEQUENCE: 105

Gln Gln His Tyr Thr Thr Pro Pro Thr
1               5

<210> SEQ ID NO 106
<211> LENGTH: 5
<212> TYPE: PRT
<213> ORGANISM: Artificial Sequence
<220> FEATURE:
<223> OTHER INFORMATION: Adalimumab CDR H1

<400> SEQUENCE: 106
```

-continued

```
Asp Tyr Ala Met His
1               5

<210> SEQ ID NO 107
<211> LENGTH: 17
<212> TYPE: PRT
<213> ORGANISM: Artificial Sequence
<220> FEATURE:
<223> OTHER INFORMATION: Adalimumab CDR H2

<400> SEQUENCE: 107

Ala Ile Thr Trp Asn Ser Gly His Ile Asp Tyr Ala Asp Ser Val Glu
1               5                   10                  15

Gly

<210> SEQ ID NO 108
<211> LENGTH: 12
<212> TYPE: PRT
<213> ORGANISM: Artificial Sequence
<220> FEATURE:
<223> OTHER INFORMATION: Adalimumab CDR H3

<400> SEQUENCE: 108

Val Ser Tyr Leu Ser Thr Ala Ser Ser Leu Asp Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Adalimumab CDR L1

<400> SEQUENCE: 109

Arg Ala Ser Gln Gly Ile Arg Asn Tyr Leu Ala
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Adalimumab CDR L2

<400> SEQUENCE: 110

Ala Ala Ser Thr Leu Gln Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Adalimumab CDR L3

<400> SEQUENCE: 111

Gln Arg Tyr Asn Arg Ala Pro Tyr Thr
1               5

<210> SEQ ID NO 112
<211> LENGTH: 10
<212> TYPE: PRT
<213> ORGANISM: Artificial Sequence
<220> FEATURE:
<223> OTHER INFORMATION: Basiliximab CDR H1
```

```
<400> SEQUENCE: 112

Gly Tyr Ser Phe Thr Arg Tyr Trp Met His
1               5                   10

<210> SEQ ID NO 113
<211> LENGTH: 17
<212> TYPE: PRT
<213> ORGANISM: Artificial Sequence
<220> FEATURE:
<223> OTHER INFORMATION: Basiliximab CDR H2

<400> SEQUENCE: 113

Ala Ile Tyr Pro Gly Asn Ser Asp Thr Ser Tyr Asn Gln Lys Phe Glu
1               5                   10                  15

Gly

<210> SEQ ID NO 114
<211> LENGTH: 8
<212> TYPE: PRT
<213> ORGANISM: Artificial Sequence
<220> FEATURE:
<223> OTHER INFORMATION: Basiliximab CDR H3

<400> SEQUENCE: 114

Asp Tyr Gly Tyr Tyr Phe Asp Phe
1               5

<210> SEQ ID NO 115
<211> LENGTH: 10
<212> TYPE: PRT
<213> ORGANISM: Artificial Sequence
<220> FEATURE:
<223> OTHER INFORMATION: Basiliximab CDR L1

<400> SEQUENCE: 115

Ser Ala Ser Ser Ser Arg Ser Tyr Met Gln
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Basiliximab CDR L2

<400> SEQUENCE: 116

Asp Thr Ser Lys Leu Ala Ser
1               5

<210> SEQ ID NO 117
<211> LENGTH: 7
<212> TYPE: PRT
<213> ORGANISM: Artificial Sequence
<220> FEATURE:
<223> OTHER INFORMATION: Basiliximab CDR L3

<400> SEQUENCE: 117

His Gln Arg Ser Ser Tyr Thr
1               5

<210> SEQ ID NO 118
<211> LENGTH: 10
<212> TYPE: PRT
<213> ORGANISM: Artificial Sequence
<220> FEATURE:
<223> OTHER INFORMATION: Belimumab CDR H1
```

<400> SEQUENCE: 118

Gly Gly Thr Phe Asn Asn Asn Ala Ile Asn
1               5                   10

<210> SEQ ID NO 119
<211> LENGTH: 17
<212> TYPE: PRT
<213> ORGANISM: Artificial Sequence
<220> FEATURE:
<223> OTHER INFORMATION: Belimumab CDR H2

<400> SEQUENCE: 119

Gly Ile Ile Pro Met Phe Gly Thr Ala Lys Tyr Ser Gln Asn Phe Gln
1               5                   10                  15

Gly

<210> SEQ ID NO 120
<211> LENGTH: 14
<212> TYPE: PRT
<213> ORGANISM: Artificial Sequence
<220> FEATURE:
<223> OTHER INFORMATION: Belimumab CDR H3

<400> SEQUENCE: 120

Ser Arg Asp Leu Leu Leu Phe Pro His His Ala Leu Ser Pro
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Belimumab CDR L1

<400> SEQUENCE: 121

Gln Gly Asp Ser Leu Arg Ser Tyr Tyr Ala Ser
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Belimumab CDR L2

<400> SEQUENCE: 122

Gly Lys Asn Asn Arg Pro Ser
1               5

<210> SEQ ID NO 123
<211> LENGTH: 11
<212> TYPE: PRT
<213> ORGANISM: Artificial Sequence
<220> FEATURE:
<223> OTHER INFORMATION: Belimumab CDR L3

<400> SEQUENCE: 123

Ser Ser Arg Asp Ser Ser Gly Asn His Trp Val
1               5                   10

<210> SEQ ID NO 124
<211> LENGTH: 10
<212> TYPE: PRT
<213> ORGANISM: Artificial Sequence
<220> FEATURE:

<223> OTHER INFORMATION: Daclizumab CDR H1

<400> SEQUENCE: 124

Gly Tyr Thr Phe Thr Ser Tyr Arg Met His
1               5                   10

<210> SEQ ID NO 125
<211> LENGTH: 17
<212> TYPE: PRT
<213> ORGANISM: Artificial Sequence
<220> FEATURE:
<223> OTHER INFORMATION: Daclizumab CDR H2

<400> SEQUENCE: 125

Tyr Ile Asn Pro Ser Thr Gly Tyr Thr Glu Tyr Asn Gln Lys Phe Lys
1               5                   10                  15

Asp

<210> SEQ ID NO 126
<211> LENGTH: 7
<212> TYPE: PRT
<213> ORGANISM: Artificial Sequence
<220> FEATURE:
<223> OTHER INFORMATION: Daclizumab CDR H3

<400> SEQUENCE: 126

Gly Gly Gly Val Phe Asp Tyr
1               5

<210> SEQ ID NO 127
<211> LENGTH: 10
<212> TYPE: PRT
<213> ORGANISM: Artificial Sequence
<220> FEATURE:
<223> OTHER INFORMATION: Daclizumab CDR L1

<400> SEQUENCE: 127

Ser Ala Ser Ser Ser Ile Ser Tyr Met His
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Daclizumab CDR L2

<400> SEQUENCE: 128

Thr Thr Ser Asn Leu Ala Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Daclizumab CDR L3

<400> SEQUENCE: 129

His Gln Arg Ser Thr Tyr Pro Leu Thr
1               5

<210> SEQ ID NO 130
<211> LENGTH: 6
<212> TYPE: PRT
<213> ORGANISM: Artificial Sequence

```
<220> FEATURE:
<223> OTHER INFORMATION: Infliximab CDR H1

<400> SEQUENCE: 130

Ile Phe Ser Asn His Trp
1               5

<210> SEQ ID NO 131
<211> LENGTH: 10
<212> TYPE: PRT
<213> ORGANISM: Artificial Sequence
<220> FEATURE:
<223> OTHER INFORMATION: Infliximab CDR H2

<400> SEQUENCE: 131

Arg Ser Lys Ser Ile Asn Ser Ala Thr His
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Infliximab CDR H3

<400> SEQUENCE: 132

Asn Tyr Tyr Gly Ser Thr Tyr
1               5

<210> SEQ ID NO 133
<211> LENGTH: 7
<212> TYPE: PRT
<213> ORGANISM: Artificial Sequence
<220> FEATURE:
<223> OTHER INFORMATION: Infliximab CDR L1

<400> SEQUENCE: 133

Phe Val Gly Ser Ser Ile His
1               5

<210> SEQ ID NO 134
<211> LENGTH: 7
<212> TYPE: PRT
<213> ORGANISM: Artificial Sequence
<220> FEATURE:
<223> OTHER INFORMATION: Infliximab CDR L2

<400> SEQUENCE: 134

Lys Tyr Ala Ser Glu Ser Met
1               5

<210> SEQ ID NO 135
<211> LENGTH: 5
<212> TYPE: PRT
<213> ORGANISM: Artificial Sequence
<220> FEATURE:
<223> OTHER INFORMATION: Infliximab CDR L3

<400> SEQUENCE: 135

Gln Ser His Ser Trp
1               5

<210> SEQ ID NO 136
<211> LENGTH: 10
<212> TYPE: PRT
<213> ORGANISM: Artificial Sequence
<220> FEATURE:
```

-continued

```
<223> OTHER INFORMATION: Natalizumab CDR H1

<400> SEQUENCE: 136

Gly Phe Asn Ile Lys Asp Thr Tyr Ile His
1               5                   10

<210> SEQ ID NO 137
<211> LENGTH: 17
<212> TYPE: PRT
<213> ORGANISM: Artificial Sequence
<220> FEATURE:
<223> OTHER INFORMATION: Natalizumab CDR H2

<400> SEQUENCE: 137

Arg Ile Asp Pro Ala Asn Gly Tyr Thr Lys Tyr Asp Pro Lys Phe Gln
1               5                   10                  15

Gly

<210> SEQ ID NO 138
<211> LENGTH: 14
<212> TYPE: PRT
<213> ORGANISM: Artificial Sequence
<220> FEATURE:
<223> OTHER INFORMATION: Natalizumab CDR H3

<400> SEQUENCE: 138

Glu Gly Tyr Tyr Gly Asn Tyr Gly Val Tyr Ala Met Asp Tyr
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Natalizumab CDR L1

<400> SEQUENCE: 139

Lys Thr Ser Gln Asp Ile Asn Lys Tyr Met Ala
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Natalizumab CDR L2

<400> SEQUENCE: 140

Tyr Thr Ser Ala Leu Gln Pro
1               5

<210> SEQ ID NO 141
<211> LENGTH: 8
<212> TYPE: PRT
<213> ORGANISM: Artificial Sequence
<220> FEATURE:
<223> OTHER INFORMATION: Natalizumab CDR L3

<400> SEQUENCE: 141

Leu Gln Tyr Asp Asn Leu Trp Thr
1               5
```